United States Patent
Ross et al.

(10) Patent No.: US 7,030,230 B2
(45) Date of Patent: Apr. 18, 2006

(54) PROCESS OF PURIFYING PHOSPHORAMIDITES

(75) Inventors: Bruce Ross, Carlsbad, CA (US); Quanlai Song, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 313 days.

(21) Appl. No.: 10/280,383

(22) Filed: Oct. 25, 2002

(65) Prior Publication Data

US 2004/0082775 A1   Apr. 29, 2004

(51) Int. Cl.
*C07H 21/04* (2006.01)
*C07H 19/04* (2006.01)

(52) U.S. Cl. .................. 536/16.1; 536/27; 544/243; 544/244

(58) Field of Classification Search ............... 536/26.1, 536/27; 544/243, 244
See application file for complete search history.

(56) References Cited

U.S. PATENT DOCUMENTS

| | | | |
|---|---|---|---|
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,973,679 A | 11/1990 | Caruthers et al. | 536/27 |
| 5,026,838 A * | 6/1991 | Nojiri et al. | 536/25.34 |
| 5,132,418 A | 7/1992 | Caruthers et al. | 536/27 |
| RE34,069 E | 9/1992 | Köster et al. | 536/27 |
| 5,646,265 A | 7/1997 | McGee | 536/25.34 |
| 5,705,621 A | 1/1998 | Ravikumar | 536/23.1 |
| 5,847,106 A | 12/1998 | Ravikumar et al. | 536/25.34 |
| 5,955,600 A | 9/1999 | Griffey et al. | 536/25.34 |
| 6,001,982 A | 12/1999 | Ravikumar et al. | 536/22.1 |
| 6,124,450 A | 9/2000 | Ravikumar et al. | 536/25.34 |
| 6,133,438 A | 10/2000 | Cook et al. | 536/25.34 |
| 6,160,152 A | 12/2000 | Capaldi et al. | 558/70 |
| 6,274,725 B1 | 8/2001 | Sanghvi et al. | 536/25.34 |
| 6,329,519 B1 | 12/2001 | Collingwood et al. | 536/25.34 |
| 6,335,439 B1 | 1/2002 | Eleuteri et al. | 536/25.34 |

OTHER PUBLICATIONS

Beaucage, S.L., et al., "Oligodeoxyribonucleotides synthesis," Agrawal, S. (Ed.), *Methods in Molecular Biology*, 1993, 20(3), 33-61

Froehler, B.C., et al., "Oligodeoxynucleotide synthesis," Agrawal, S. (Ed.), *Methods in Molecular Biology*, 1993, 20, Chapter 4, 63-80.

* cited by examiner

*Primary Examiner*—James O. Wilson
*Assistant Examiner*—Ganapathy Krishnan
(74) *Attorney, Agent, or Firm*—ISIS Patent Department Woodcock Washburn LLP

(57) ABSTRACT

A process of purifying phosphoramidite precursors useful in inter alia synthesis of oligonucleotides comprises dissolving a crude phosphoramidite in a polar phase, adding a basic compound to the polar phase, adding a portion of water to the polar phase, contacting the polar phase with a first apolar phase to extract impurity into the apolar phase, separating the first apolar phase from the polar phase, adding a second aliquot of water to the polar phase, and contacting the polar phase with a second apolar phase, whereby the phosphoramidite partitions into the second apolar phase.

73 Claims, No Drawings

PROCESS OF PURIFYING PHOSPHORAMIDITES

FIELD OF THE INVENTION

The present invention is directed to the field of synthetic organic chemistry. In particular the present invention provides an improved method of purifying phosphoramidite compounds, and methods of using purified phosphoramidites to make compounds containing phosphodiester, phosphorothioate and phosphorodithioate containing compounds.

BACKGROUND OF THE INVENTION

Proteins, acting directly or through their enzymatic functions, contribute in major proportion to many diseases in animals and man. Classical therapeutic methods have generally focused on modulating protein function with exogenous compounds that interact with proteins, with the goal of moderating their disease-causing or disease-potentiating functions. Recently, however, attempts have been made to moderate the actual production of certain proteins using molecules that direct protein synthesis, such as intracellular RNA. By interfering with the production of proteins, it has been hoped to effect therapeutic results with maximal desired effect and minimal side effects. It is the general object of such therapeutic approaches to interfere with, or otherwise modulate, the expression of genes that lead to undesired protein formation.

One method for inhibiting specific gene expression is the use of oligonucleotides and oligonucleotide analogs as "antisense" agents. Antisense technology involves directing oligonucleotides, or analogs thereof, to a specific, target messenger RNA (mRNA) sequence, whereby transcription is modulated. Thus, antisense technology permits modulation of essential functions of intracellular nucleic acids.

As antisense oligonucleotides and oligonucleotide analogs are now accepted as therapeutic agents holding great promise for therapeutic and diagnostic methods, it has become desirable to produce them in relatively large quantities. In some applications, it is necessary to produce large numbers of small batches of diverse oligonucleotides or their analogs for screening purposes. In other cases, for example in the production of therapeutic quantities of oligonucleotides and their analogs, it is necessary to make large batches of the same oligonucleotide, or analog thereof.

Three principal methods have been used for the synthesis of oligonucleotides. The phosphotriester method, as described by Reese, *Tetrahedron* 1978, 34, 3143; the phosphoramidite method, as described by Beaucage, in *Methods in Molecular Biology: Protocols for Oligonucleotides and Analogs*; Agrawal, ed.; Humana Press: Totowa, 1993, Vol. 20, 33–61; and the H-phosphonate method, as described by Froehler in *Methods in Molecular Biology: Protocols for Oligonucleotides and Analogs* Agrawal, ed.; Humana Press: Totowa, 1993, Vol. 20, 63–80. Of these three methods, the phosphoramidite method has become a defacto standard in the industry.

In order to meet in the increasing demand for oligonucleotides and their analogs, it increasingly necessary to produce the intermediates for oligonucleotide synthesis in greater quantity, and with satisfactory purity, to satisfy the increased demand for the final products. In the case of phosphoramidite synthesis, it is desirable to scale up the process of making phosphoramidite precursors. As impurities in phosphoramidite precursors will impact oligonucleotide product purity, the phosphoramidite must be of exceptional purity. However, the classical methods of purifying phosphoramidites, involving purification on silica gel columns, are less than suitable for scale up. Larger scale purification requires the use of larger silica gel columns, which in turn results in increased residence time on the silica gel columns, and increased volumes of mobile phase solvent. As phosphoramidites tend to degrade in a time-wise manner on silica gels, large volume silica gel columns mean greater proportional loss of the desired product and a concomitant increase in undesirable contaminants. One of the results of scale-up of phosphoramidite purification on silica gels is thus a decrease in percent product yield, which tends to offset any advantages of scale that have been realized at other steps in the synthesis.

Another result of scale-up is an increase in time required to remove solvent from the product. As column volume increases, diffusion causes an increase in fraction volume, a large portion of which is simply mobile phase solvent. While solvent stripping may be a minor consideration in small-scale purification, it can require substantial amounts of time as scale increases.

Of course, increased column volume, and the resulting increase in product fraction volume, result in greater expenditures of operator time.

There is thus a need for a scalable, economic process for purifying phosphoramidites that avoids the problems of phosphoramidite degradation and solvent usage associated with conventional silica gel column purification.

SUMMARY OF THE INVENTION

The foregoing and other needs are met by embodiments of the present invention, which provide a process of purifying a phosphoramidite, the process comprising:

(a) providing a crude phosphoramidite in a polar phase, the polar phase comprising a polar organic solvent and at least one impurity;

(b) adding a basic compound to the polar phase;

(c) adding a first portion of water to the polar phase;

(d) contacting the polar phase with a first apolar phase;

(e) separating the first apolar phase from the polar phase;

(f) adding a second portion of water to the polar phase;

(g) contacting the polar phase with a second apolar phase, whereby the phosphoramidite partitions into the second apolar organic phase; and (h) separating the polar phase from the second apolar phase.

The foregoing and further needs are met by embodiments of the present invention, which provide a process of purifying a phosphoramidite, the process comprising:

(a) providing a crude phosphoramidite in a polar phase, the polar phase initially comprising a polar organic solvent and at least one impurity;

(b) adding a basic compound to the polar phase;

(c) adding a first portion of water to the polar phase;

(d) contacting the polar phase with a first apolar phase;

(e) separating the first apolar phase from the polar phase;

(f) adding a second portion of water to the polar phase;

(g) contacting the polar phase with a second apolar phase, whereby the phosphoramidite partitions into the second apolar organic phase;

(h) separating the polar phase from the second apolar phase; and (i) subjecting the second apolar phase to one or more additional steps selected from the group of:

a. solvent stripping, b. back extraction, c. gumming out, and d. drying.

The purified phosphoramidites according to the present invention are advantageously used in the phosphoramidite method of synthesizing oligonucleotides, including phosphodiester, phosphorothioate and phosphorodithioate oligonucleotides.

DETAILED DESCRIPTION OF THE INVENTION

The present invention provides an improved process of purifying a phosphoramidite compound, such as a phosphoramidite nucleoside. Such compounds are especially useful in the in synthesis of oligonucleotides.

The present inventors have found that phosphoramidites (also known simply as amidites) may be purified by a two-stage extraction process. In the first stage, phosphoramidites are separated from less polar impurities by first dissolving the phosphoramidite in a polar solvent to form a polar phase that contains impurities, after which a basic compound is added to the polar phase, and an aliquot of water is added to increase the polarity of the polar phase. The polar phase is then contacted with a first apolar phase, and impurities that are more apolar than the phosphoramidite partition from the polar phase into the first apolar phase. The first apolar phase is then separated from the polar phase, the desired phosphoramidite compound being left in the polar phase.

In the second stage of purification, a second aliquot of water is added to the polar phase. This has the effect of making the polar phase even more polar. The polar phase is then contacted with a second apolar phase, whereby the phosphoramidite partitions from the polar phase into the second apolar phase. Impurities that are more polar than the phosphoramidite are left in the polar phase.

The second apolar phase, which contains the desired product, can then be separated from the polar phase. The second apolar phase can then be subjected to one or more additional steps for purification, such as back-extraction, drying, solvent stripping or by gumming out.

The phosphoramidite produced by embodiments of the process according to the present invention has excellent purity and is produced in superior yield as compared to phosphoramidite purified by the conventional process of silica gel column purification. Additionally, phosphoramidite may be purified by embodiments of the process according to the present invention using much less solvent than would be required on a similar scale by the conventional silica gel chromatography purification methods.

The starting material for the purification process according to the present invention is a crude phosphoramidite. A crude phosphoramidite is a mixture of phosphoramidite and at least one impurity, and in most cases, a plurality of impurities. In some embodiments of the invention, the crude phosphoramidite comprises phosphoramidite, at least one impurity that is more polar than the phosphoramidite, and at least one impurity that is less polar than phosphoramidite. Impurities found in crude phosphoramidite include side products of reactions used to make the phosphoramidite, impurities inherent in the starting materials used to make the phosphoramidite and precursors thereto, impurities inherent in the solvents and reagents used to make the phosphoramidite, degradation products, and other impurities that may arise in making the phosphoramidite. Specific impurities include capped phosphorus impurities (e.g. compounds of the formula:

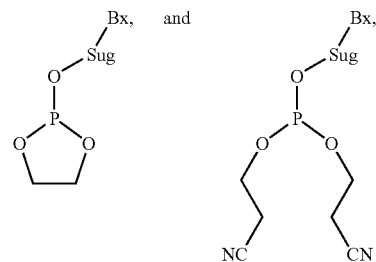

wherein Sug is a sugar ring or an analog thereof, which may be substituted and Bx is a nucleobase, each as described in greater detail herein.

In general, a phosphoramidite according to the present invention is a compound having the formula:

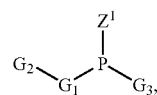

wherein $G_1$ is selected from O and S, $G_2$ is an O or S protective group, $G_3$ is an amino leaving group and $Z^1$ is an organic moiety, such as a monomer or oligomer subunit as described in more detail herein. In some embodiments of the present invention, the moiety $Z^1$ is has the structure: -Sug-Bx, wherein Sug and Bx have the meanings defined herein.

Thus the term phosphoramidite (or simply amidite) has the meaning of the desired product, which product may be used, inter alia in the synthesis of oligonucleotides having a phosphodiester, phosphorothioate or phosphorodithioate backbone. When used without qualification in the context of the present invention, phosphoramidite is intended to encompass both purified phosphoramidite and crude phosphoramidite. When used with the additional modifier "crude," it is intended to be limited to phosphoramidite having one or more impurities mixed therewith, the term "impurity" being defined herein. When used with the additional modifier "purified," it is intended to be limited to phosphoramidite that has been subjected to at least one cycle of the two-stage process according to the present invention, as that process is described herein.

The present invention provides a new, general process for synthesizing and purifying nucleoside phosphoramidites without silica gel chromatography. In methods common in the art, a 10 kg batch of phosphoramidite would be considered very large, and would require a pressurized chromatography system costing several hundred thousand dollars. On a research scale (10–100 g), a typical yield for phosphoramidites purified by chromatography would be 80%, which would be acceptable. However, on a kilogram-scale run, particularly with more sensitive products such as 2'-O-(2-methoxyethyl)-guanosine (as noted below) the prior art yield can fall to 50–65%, which is not generally acceptable, as the reduced yields tend to offset any economies of scale that may have been obtained in other steps of the process.

The present invention provides a general process for synthesizing and purifying nucleoside phosphoramidites without the disadvantages presented by silica gel chromatography. In particular, the inventive method avoids problems, such as low yield, high solvent uses, high man-hour demand, pressurized systems, etc. that are normally associated with large scale column chromatography. Although the invention is generally useful at any scale, it is particularly suitable for large-scale purification, e.g. at scales above 100 g batch sizes, and in particular above about 300 g batch sizes, e.g. on multi-kilogram runs, especially the range of about 20 to about 40 Kg batch sizes. The method provides yields that are generally in the 95% range. The method generally results in product purity, as judged by reactive impurities in the 145–170 ppm range of phosphorus NMR that is as good as, or better than, the typical purity of a column-purified phosphoramidite batch. The inventive method also results in reductions in solvent usage and man-hour expenditure relative to the prior art chromatographic purification methods.

Production of crude phosphoramidite is depicted in the equation below:

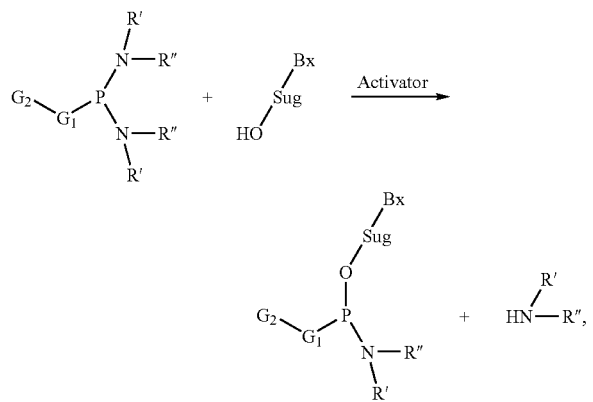

wherein $G_1$, $G_2$, NR'R", Sug, and Bx are defined herein.

The reaction may be carried out in a variety of solvents. In some embodiments of the invention, the reaction conditions are optimized to facilitate later purification by the inventive process. For example, DMF (dimethylformamide), dichloromethane (DCM) and acetonitrile are suitable polar phase solvents for the inventive method. In particular embodiments, DMF is a preferred solvent in the later extraction work-up, so DMF is also chosen as a preferred reaction solvent. Another advantage to using DMF is that protected nucleosides are very soluble in it, so the reaction can be carried out in a highly concentrated solution and the equipment can be used more efficiently. In other embodiments of the invention, acetonitrile may advantageously be used as the reaction solvent, as discussed in more detail herein.

It is generally advantageous to use a catalyst (activator) in the foregoing reaction. One standard activator is tetrazole. Other suitable activators include a combination of tetrazole and N-methylimidazole, N-methylimidazole (NMI) and salts thereof. Suitable NMI salts include the trifluoroacetate, trifluoromethanesulfonate, dichloroacetate, trichloroacetate, tetrafluoroborate salts of NMI, and trifluoromethane sulfonate (triflate). A suitable replacement for tetrazole is ethylthiotetrazole. Other suitable activators include dicyanoimidazole (DCI). Of the above, NMI/tetrazole, NMI trifluoroacetate and NMI trifluoromethane sulfonate are preferred. The latter two salts have resulted in slightly faster reactivity than NMI/tetrazole. The person skilled in the art will recognize that it is advantageous for the activator to be removable in the aqueous extraction step. Activators may be used at various concentrations; a ratio of approximately one equivalent per equivalent of amidite is acceptable. Where the activator is used as a salt, the ratio of activator to counter ion may vary; a ratio of approximately 1:1 is acceptable. Accordingly, it is expected that the person skilled in the art will choose an appropriate activator according to the foregoing description. Other suitable activators may be found in U.S. Pat. No. 6,031,092, which is incorporated herein by reference.

In some cases, the molar ratio of phosphitylation reagent (phos reagent) to protected nucleoside (PNS) may be important. The present inventors have found that a stoichiometric excess of phos reagents to PNS should be used in order to ensure efficient production of the target amidite. In some embodiments, a ratio of 1.5:1 (phos reagent: PNS) or greater has been shown to suppress the formation of nucleoside dimer side-products. Excess reagent can be removed by the process according to the present invention. In some embodiments, a ratio in the range of about 1.2:1 to about 1.4:1 will suffice. These ratios are exemplary only. Other ratios may be advantageously employed in alternative embodiments of the invention, and such ratios are contemplated as being within the broad scope of the present invention. The person having skill in the art will appreciate that the choice of stoichiometric ratio will depend upon considerations of reagent economy; optimization of amidite yields, purification times, etc., and will adjust the ratio in accordance with these considerations.

In the process of the present invention, a solution containing the crude phosphoramidite produced in the reaction above, in a suitable solvent, is first basified with a suitable base, such as triethylamine, N-methyl piperidine, pyridine, etc., and is then diluted with a small portion of water. The resulting solution is referred to herein as the polar phase. (This is in contrast to the typical prior art process, wherein the phosphitylation reaction is quenched with water, whereby excess phosphitylation reagent is instantly hydrolyzed to its H-phosphonate, which is a side-product that has similar polarity to the desired nucleoside products and is often difficult to remove by extraction.) The present inventors have discovered that the phosphitylation reagent is stable to water under basic conditions, which facilitates its removal from the phosphoramidite by the process of the present invention. After the solution is basified, the mixture is extracted with a first apolar solvent, such as hexanes, to remove the excess of the phosphorodiamidite reagent and other lipophilic impurities, while the desired products, being relatively insoluble in these lipophilic solvents, remain in the polar phase (e.g. basified aqueous/DMF phase). In some embodiments, hexanes are replaced with other relatively apolar solvents, such as heptane, cyclohexane, methylcyclohexane, or other non-polar organic solvents.

After the first apolar phase is removed from contact with the polar phase, the polar phase is further diluted with water to increase its polarity, thereby making the phosphoramidite product relatively less soluble therein. The desired product is then extracted with a second apolar phase, such as a mixture of toluene and hexane, isopropyl ether, t-butyl methyl ether, etc. The products are extracted into the second apolar layer, while the impurities that are more polar than the phosphoramidite are concentrated in the polar phase.

Both ratios of toluene to hexane and DMF to water may be optimized for each particular phosphoramidite (e.g. for each particular Sug-Bx). The ratio of toluene to hexane may be adjusted to dissolve the maximum amount of phosphoramidite product, and the minimum amount of impurities, while the aqueous DMF layer may be optimized to efficiently solubilize polar impurities and not the phosphoramidite product.

After the polar phase is separated from the second apolar phase, the second apolar phase, which contains the desired, purified, product, may be further extracted with a polar wash having polarity similar to, or greater than, the polar phase above. For example, the polar wash may comprise aqueous DMF having the same ratio of water to DMF and base as the above polar phase.

The second apolar phase may also be extracted with water to wash away any remaining polar organic solvent, such as DMF, acetonitrile, etc. As the polar and apolar phases form discrete lower and upper layers, respectively, the extraction can be easily monitored by phosphorus NMR of both the upper and lower layers. The ratios of toluene to hexane is suitably in the range of 50:50 to 80:20 (v/v) and the ratio of DMF to water is also suitably in the range of 50:50 to 80:20 (v/v). Optimal ratios are dependent on the nature of the nucleoside (e.g. the nucleobase, Bx, and the sugar or sugar mimetic) portion of the phosphoramidite, as well as on the choice of solvents. Toluene can be replaced, in whole or in part, by xylene, ethyl benzene, and other water immiscible solvents of similar polarity. DMF can be replaced by N-methylacetamide, 2-pyrrolidinone, ethylene glycol, and other water miscible solvents of similar polarity, such as acetonitrile.

The second apolar phase, e.g. the above toluene layer, isopropyl ether, or t-butyl methyl ether, may be removed from the purified phosphoramidite, for example by evaporation. In particular embodiments of the invention, the second apolar phase solvent, e.g. toluene, may be evaporated under reduced pressure to give the amidite product as a solid. In some embodiments, the amidite product may be further purified by precipitation. In an exemplary precipitation procedure, the amidite is dissolved in a relatively small volume of a relatively polar solvent to form a polar amidite solution, which is then added quickly to a large volume of non-polar solvent. The sudden change in polarity causes the amidite product to form a solid that quickly precipitates, or "crashes out" of solution. While it is desirable in some cases to form such a solid, this method does not result in much purification, as intermediate polarity impurities can preferentially associate with the polar amidite product rather than the non-polar solvent.

Whether the amidite product is worked up by the foregoing precipitation procedure or not, some intermediate polarity impurities, such as N,N-diisopropyl-bis-(2-cyanoethyl)amidite (DCEA), may remain in the product. The product quality may be improved by what is referred to herein as a "reverse precipitation" procedure. This procedure is also known as "gumming out," for reasons that will become clear hereafter. In suitable embodiments, the an amidite product residue comprising one or more intermediate polarity impurities may be dissolved in a volume of a first, slightly polar non-aqueous solvent, such as toluene (or another alkylated benzene solvent), after which about 1–20 volumes of a second non-aqueous solvent of slightly lower polarity, e.g. and alkane solvent, such as hexane or heptane, is gradually added, with agitation, until the phosphoramidite product forms a gum layer that is discrete from the organic solvent layer comprising the slightly polar organic solvent and the apolar organic solvent. (The skilled artisan will appreciate that the slightly polar organic solvent and the apolar organic should be miscible). The organic solvent is then separated from the gum phase, e.g. by decanting, thereby isolating the phosphoramidite product. The same gumming out process may be repeated, if necessary, by dissolving the gum phase in a slightly polar organic solvent, gradually adding apolar organic solvent, etc. In some embodiments of the invention, the crude product is dissolved in one volume of toluene, to which about 1–2 volumes of hexane are gradually added with agitation. The gradual addition of non-polar organic solvent gradually changes the polarity of the solvent system until the amidite product is no longer soluble in the organic solvent, at which point the product forms a second, discrete, gum-like, phase. Intermediate polarity impurities, such as the aforementioned DCEA, will tend to remain in the organic solvent phase, which may be removed by a suitable method, such as by decanting off the organic solvent.

The reverse precipitation procedure provides advantages when compared to the previously described precipitation scheme (i.e. wherein a crude product is dissolved in a minimum volume of a slightly polar solvent (e.g. dichloromethane) and then quickly added about 100 volumes of hexane, whereby a filterable solid product is obtained.) Surprisingly, despite the apparent disadvantage of providing a gummy product (contrasted with the filterable solid product provided by the precipitation procedure), the reverse precipitation procedure of the present invention provides for removal of intermediate polarity impurities, resulting in a purer final product.

In some embodiments according to the invention, the gum may then be redissolved in solvent, such as acetonitrile, and the solution evaporated and dried to give the final product.

A variety of solvents and solvent combinations can be used for this "gumming out" procedure. The present inventors have found that toluene is more efficient and efficacious than dichloromethane or ethyl acetate, although any number of apolar solvents may be used in the work-up of purified phosphoramidite.

The precipitation and reverse precipitation procedures may also be combined in a work-up scheme, in any suitable order. The person skilled in the art will recognize that other suitable work up procedures may be practiced within various embodiments of the present invention. The choice of precipitation, reverse precipitation, or a combination of the two work-up techniques will depend in part upon the batch size. In general, precipitation is more suitable for larger-scale batches, whereas the gumming out is more suitable for small to medium size batches. However, the person skilled in the art will recognize that modifications of the procedures may be made to accommodate different batch sizes, and such modifications are contemplated as being within the ordinary skill in the art.

The present invention includes at least one step requiring the use of polar phase solvents. Suitable polar phase solvents include acetaldehyde, N-acetyl-N-methylacetamide, N,N-dimethylacetamide, acetonitrile, 1,4-butanediol, 2,3-butanediol, 2-amino-1-butanol, 1,3-dioxane, 1,4-dioxane, ethylene glycol, ethylene glycol monoacetate, diethylene glycol diethyl ether, ethanol, 2-butoxyethanol, 2-bromoethanol, diethylene glycol monobutyl ether, 2-chloroethanol, 2-methoxyethanol, 2-isopropoxyethanol, 2-nitroethanol, N,N-dimethylformamide, N,N-diethylformamide, 2-furanmethanol, dihydro-5-methyl-2(3H)-furanone, 5-methyl-2(3H)-furanone, 1,2-dimethylhydrazine, methanol, 1,3-propanediol, 1,2-propanediol, 2-hydroxypropanenitrile, 3-hydroxypropanenitrile, glycerol, glyceroltrimethylether, 1-propanol, 2-propanol, 1,3-dimethoxy-2-propanol, 1-chloro-2-propanol, dipropyleneglycol, 2-propen-1-ol.

Bases for adjusting the pH of the polar phase solvent include aziridine, benzylamine, 3-methyl-1-butanamine, ethanamine, diethylenetriamine, N-(aminoethyl)ethanolamine, ethanolamine, N,N-diisobutylethanolamine, triethanolamine, N-methyl-2-ethanolamine, 2-[(1-methylethyl)amino]ethanol, 2-furanmethanamine, morpholine, N-ethylmorpholine, 2,6-dimethylmorpholine, 5-amino-2-pentanol, tert-butylamine, 1-amino-2-propanol, 2-propen-1-amine, 2,6-dimethylpyridine, 3-methyl-1H-pyrazole, 3-picoline, 4-picoline.

Apolar phase solvents suitable for use in the methods according to the present invention include hexane, heptane, octane, nonane, benzene, toluene, p-xylene, o-xylene, m-xylene, mineral spirits, and mixtures thereof.

The present invention is concerned with the general problem of manufacturing starting materials for the manufacture of oligonucleotides and their analogs. In general, the present invention addresses challenges facing the oligonucleotide manufacturing industry, such as purity of oligonucleotide products and costs of oligonucleotide manufacturing processes. The inventive process may also be used, under suitable conditions, to make chimeric products. The term "chimeric products" includes oligomers having at least a first portion comprising at least two nucleosides joined to one another by a phosphate diester or phosphorothioate diester linker, and at least one other portion conjugated to the first portion. The first portion is referred to herein as the oligonucleotide portion, while the second portion is referred to as the conjugate portion. The conjugate portion may include oligomeric moieties other than oligonucleotides, as well as other organic moieties. The other organic moieties include fatty acids, monomeric or polymeric sugars, peptides, proteins, and other moieties that impart useful properties to the overall oligomeric structure.

In the context of the invention, the terms "oligomeric compound" and "oligomer" refer to a polymeric structure capable of hybridizing a region of a nucleic acid molecule. These terms include oligonucleotides, oligonucleosides, oligonucleotide analogs, modified oligonucleotides and oligonucleotide mimetics. Oligomeric compounds can be linear or circular and may include branching. They can be single-stranded or double-stranded, and when double-stranded, may include overhangs. An oligomeric compound comprises a backbone of monomeric subunits that share some common structural feature, where each monomeric subunit is linked to an adjacent monomeric subunit by an appropriate linker. Each monomeric subunit is directly or indirectly attached to a heterocyclic base moiety. The linkages joining the monomeric subunits to one another, the monomeric subunits, and the heterocyclic base moieties, can all vary in structure, giving rise to a plurality of motifs for the resulting oligomeric compounds including hemimers, gapmers and chimeras.

One type of monomeric subunit known in the art is a nucleoside, which is a base-sugar combination. The base portion of the nucleoside is normally a heterocyclic base moiety, or nucleobase. The two most common classes of such heterocyclic bases are purines and pyrimidines. A nucleoside having a phosphate group (or a phosphorothioate group) is called a nucleotide. When a plurality of nucleosides are linked by successive phosphate or phosphorothioate groups, the resulting oligomer is called an oligonucleotide.

In the broadest sense, the term "oligonucleotide" refers to an oligomer having a plurality of sugar units linked by phosphate diester or phosphorothioate diester moieties. In some embodiments of the invention, an oligonucleotide may contain both phosphate diester and phosphorothioate linkers. In other embodiments, the linkers are all thiophosphate linkers. While phosphate linkers are the naturally occurring type of linkers in oligonucleotides, thiophosphate linkers are known to confer stability to oligonucleotides cells. Hence, it is often preferred to prepare oligonucleotides with at least a portion of the phosphate diester moieties replaced by phosphorothioate diester moieties.

A standard oligonucleotide is shown in formula 1 below:

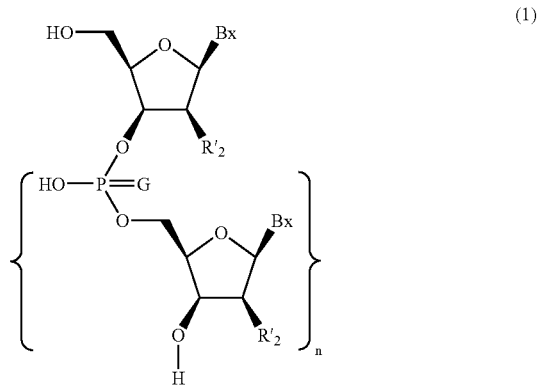

(1)

In formula 1, each G is independently O or S, each $R'_2$ is independently H or OH, n is an integer and each Bx is independently a nucleobase as described in greater detail herein. Thus the repeating backbone unit is a ribosyl ring linked to a phosphate or phosphorothioate linker. Selectivity for a particular target sequence is achieved by modification of the sequence of Bx units. This procedure is discussed in greater detail herein.

The 2'-position may be H (i.e. 2'-deoxyribosyl) or OH (ribosyl). While it is possible for all $R'_2$ units to be OH, e.g. where the oligomers will be used in siRNA applications, it is often desirable for all or part of the oligomer to be 2'-deoxy. In preferred embodiments of the present invention, each of the $R'_2$ groups is H. In other cases, a contiguous stretch sugars are 2'-deoxy, while one or more stretches of the remainder of the oligonucleotide contain ribosyl or 2'-modified ribosyl sugars, as described in more detail herein. It has been found that oligonucleotides containing a stretch of deoxy ribosyl nucleotides are able to recruit RNase H, as described in greater detail herein.

Formula 1 depicts the simplest oligonucleotides, which are also referred to in the art as "first generation" oligonucleotides. Other oligonucleotides are possible, and are encompassed within the meaning of "oligonucleotide" as used herein. In particular, oligonucleotides may contain repeating units where the standard ribosyl unit is replaced with a substituted ribosyl unit (e.g. a 2'-deoxy-2'-substituted ribosyl unit), where the ribosyl unit is replaced by a different sugar entirely (e.g. an arabinosyl or erythrosyl unit), or where the ribosyl unit is replaced by a bridged sugar unit. A general formula for an oligonucleotide of this type is depicted in Formula 2.

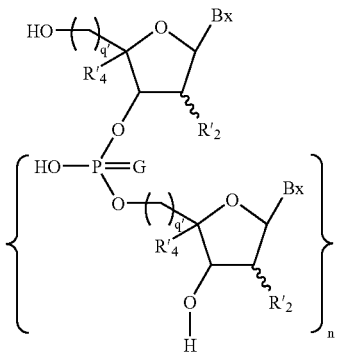

(2)

In formula 2, G, Bx and n have the same meanings as in formula 1. The squiggly line joining R'$_2$ to the ring indicates that the 2'-substituent may be in either the down or up configuration. The value of q' may be 0 or 1. R'$_2$ may be H, OH, a protected OH, a 2'-substituent, or may form, together with R'$_4$, a bridge unit. R'$_4$ is either H or, together with R'$_2$, forms a bridge.

The skilled artisan will recognize that when R'$_2$ is in the down configuration and q' is 1, the ring is a ribosyl ring, whereas when R'$_2$ is in the up configuration and q' is 1, the ring is an arabinosyl ring. Likewise, when q' is 0 and R'$_2$ is in the down configuration, the ring is an erythrosyl ring. When R'$_2$ and R'$_4$ are joined to form a bridge, the ring is called a locked nucleic acid (LNA), as described in greater detail herein. In some embodiments, the bridge formed by R'$_2$ and R'$_4$ is R'$_2$—O—(CH$_2$)$_r$—R'$_4$ (wherein r is 1 or 2) or R'$_2$—CH$_2$—O—CH$_2$—R'$_4$ (the use of R'$_2$ and R'$_4$ in the sub-formulae indicating the points of attachment.)

In its broadest sense, then, the variable Sug, as used herein, refers to a sugar ring or a modified sugar ring. Sugar rings include ribosyl, 2'-deoxyribosyl, arabinosyl, erythrosyl and other sugar rings. Modified sugar rings include the foregoing sugar rings as modified per the description herein, e.g. at the 2'-position, or by a bridge between the 2'- and 4'-positions as described in further detail herein.

The variable Bx refers to a nucleobase as described further herein.

Certain oligonucleotides that utilized arabino-pentofuranosyl nucleotides as building blocks have been described. Damha et. al., J. A. C. S., 1998, 120, 12976–12977; and Damha et. al., *Bioconjugate Chem.*, 1999, 10, 299–305.

Suitable 2'-substituents corresponding to R'$_2$ include: OH, F, O-alkyl (e.g. O-methyl), S-alkyl, N-alkyl, O-alkenyl, S-alkenyl, N-alkenyl; O-alkynyl, S-alkynyl, N-alkynyl; O-alkyl-O-alkyl, wherein the alkyl, alkenyl and alkynyl may be substituted or unsubstituted C$_1$ to C$_{10}$ alkyl or C$_2$ to C$_{10}$ alkenyl or alkynyl, respectively. Particularly preferred are O[(CH$_2$)$_g$O]$_h$CH$_3$, O(CH$_2$)$_g$OCH$_3$, O(CH$_2$)$_g$NH$_2$, O(CH$_2$)$_g$CH$_3$, O(CH$_2$)$_g$ONH$_2$, and O(CH$_2$)$_g$ON[(CH$_2$)$_g$CH$_3$]$_2$, where g and h are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred 2'-modification includes 2'-methoxyethoxy (2'—O—CH$_2$CH$_2$OCH$_3$, also known as 2'—O—(2-methoxyethyl) or 2'-MOE) (Martin et al., *Helv. Chim. Acta*, 1995, 78, 486–504). A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Other preferred modifications include 2'-methoxy (2'—O—CH$_3$), 2'-aminopropoxy (2'-OCH$_2$CH$_2$CH$_2$NH$_2$), 2'-allyl (2'-CH$_2$—CH═CH$_2$), 2'-O-allyl (2'—O—CH$_2$—CH═CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide.

Further representative substituent groups include groups of formula I$_a$ or II$_a$:

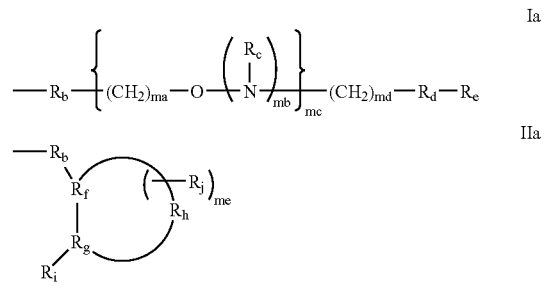

Ia

IIa wherein:

R$_b$ is O, S or NH;

R$_d$ is a single bond, O or C(═O);

R$_e$ is C$_1$-C$_{10}$ alkyl, N(R$_k$)(R$_m$), N(R$_k$)(R$_n$), N═C(R$_p$)(R$_q$), N═C(R$_p$)(R$_r$) or has formula III$_a$;

IIIa each R$_s$, R$_t$, R$_u$ and R$_v$ is, independently, hydrogen, C(O)R$_w$, substituted or unsubstituted C$_1$-C$_{10}$ alkyl, substituted or unsubstituted C$_2$-C$_{10}$ alkenyl, substituted or unsubstituted C$_2$C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_k$ is hydrogen, a nitrogen protecting group or —$R_x$—$R_y$;

$R_p$ is hydrogen, a nitrogen protecting group or —$R_x$—$R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_i)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_1$ is $OR_z$, $SR_z$, or $N(R_z)_2$;

each $R_z$ is, independently, H, $C_1$–$C_8$ alkyl, $C_1$–$C_8$ haloalkyl, $C(=NH)N(H)R_u$, $C(=O)N(H)R_u$ or $OC(=O)N(H)R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;

each mb is, independently, 0 or 1;

mc is 0 or an integer from, 1 to 10;

md is an integer from 1 to 10;

me is from 0, 1 or 2; and provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety. Representative cyclic substituent groups of Formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Particularly preferred sugar substituent groups include $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3)]_2$, where g and h are from 1 to about 10.

Some preferred oligomeric compounds of the invention contain at least one nucleoside having one of the following substituent groups: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'—O—(2-methoxyethyl) or 2'-MOE] (Martin et al., *Helv. Chim. Acta*, 1995, 78, 486), i.e., an alkoxyalkoxy group. A further preferred modification is 2'-dimethylaminooxyethoxy, i.e., a $O(CH_2)_2ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200, which is hereby incorporated by reference in its entirety. Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

While the present invention may be adapted to produce oligonucleotides for any desired end use (e.g. as probes for us in the polymerase chain reaction), one preferred use of the oligonucleotides is in antisense therapeutics. One mode of action that is often employed in antisense therapeutics is the so-called RNAse H mechanism, whereby a strand of DNA is introduced into a cell, where the DNA hybridizes to a strand of RNA. The DNA-RNA hybrid is recognized by an endonuclease, RNAse H, which cleaves the RNA strand. In normal cases, the RNA strand is messenger RNA (mRNA), which, after it has been cleaved, cannot be translated into the corresponding peptide or protein sequence in the ribosomes. In this way, DNA may be employed as an agent for modulating the expression of certain genes.

It has been found that by incorporating short stretches of DNA into an oligonucleotide, the RNAse H mechanism can be effectively used to modulate expression of target peptides or proteins. In some embodiments of the invention, an oligonucleotide incorporating a stretch of DNA and a stretch of RNA or 2'-modified RNA can be used to effectively modulate gene expression. In preferred embodiments, the oligonucleotide comprises a stretch of DNA flanked by two stretches of 2'-modified RNA. Preferred 2'-modifications include 2'-MOE as described herein.

The ribosyl sugar moiety has also been extensively studied to evaluate the effect its modification has on the properties of oligonucleotides relative to unmodified oligonucleotides. The 2'-position of the sugar moiety is one of the most studied sites for modification. Certain 2'-substituent groups have been shown to increase the lipophilicity and enhance properties such as binding affinity to target RNA, chemical stability and nuclease resistance of oligonucleotides. Many of the modifications at the 2'-position that show enhanced binding affinity also force the sugar ring into the $C_3$-endo conformation.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807–10815; Conte et al., *Nucleic Acids Res.*, 1997, 25, 2627–2634). The increased stability of RNA has been attributed to several structural features, most notably the improved base stacking interactions that result from an A-form geometry (Searle et al., *Nucleic Acids Res.*, 1993, 21, 2051–2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489–8494).

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051–2056). The structure of a hybrid duplex is intermediate between A- and B-form geometries, which may result in poor stacking interactions (Lane et al., *Eur. J. Biochem.*, 1993, 215, 297–306; Fedoroff et al., *J. Mol. Biol.*, 1993, 233, 509–523; Gonzalez et al., *Biochemistry*, 1995, 34, 4969–4982; Horton et al., *J. Mol. Biol.*, 1996, 264, 521–533). The stability of a DNA:RNA hybrid is central to antisense therapies, as the mechanism requires the binding of a modified DNA strand to an mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

Various synthetic modifications have been proposed to increase nuclease resistance, or to enhance the affinity of the antisense strand for its target mRNA (Crooke et al., *Med. Res. Rev.*, 1996, 16, 319–344; De Mesmaeker et al., *Acc. Chem. Res.*, 1995, 28, 366–374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807–10815; Conte et al., *Nucleic Acids Res.*, 1997, 25, 2627–2634). The increased stability of RNA has been attributed to several structural features, most notably the improved base stacking interactions that result from an A-form geometry (Searle et al., *Nucleic Acids Res.*, 1993, 21, 2051–2056). The presence of the 2-hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2-hydroxyl groups of RNA can form a network of water-mediated hydrogen bonds that help stabilize the RNA duplex (Egli et al., *Biochemistry*, 1996, 35, 8489–8494).

DNA:RNA hybrid duplexes, however, are usually less stable than pure RNA:RNA duplexes and, depending on their sequence, may be either more or less stable than DNA:DNA duplexes (Searle et al., *Nucleic Acids Res.*, 1993, 21, 2051–2056). The structure of a hybrid duplex is intermediate between A- and B-form geometries, which may result in poor stacking interactions (Lane et al., *Eur. J. Biochem.*, 1993, 215, 297–306; Fedoroff et al., *J. Mol. Biol.*, 1993, 233, 509–523; Gonzalez et al., *Biochemistry*, 1995, 34, 4969–4982; Horton et al., *J. Mol. Biol.*, 1996, 264, 521–533). The stability of a DNA:RNA hybrid a significant aspect of antisense therapies, as the proposed mechanism requires the binding of a modified DNA strand to a mRNA strand. Ideally, the antisense DNA should have a very high binding affinity with the mRNA. Otherwise, the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2-methoxyethoxy (MOE, 2'-OCH$_2$CH$_2$OCH$_3$) side chain (Baker et al., *J. Biol. Chem.*, 1997, 272, 11944–12000; Freier et al., *Nucleic Acids Res.*, 1997, 25, 4429–4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429–4443). 2-O-Methoxyethyl-substituted oligonucleotides also have been shown to be antisense inhibitors of gene expression with promising features for in vivo use (Martin, P., *Helv. Chim. Acta,* 1995, 78, 486–504; Altmann et al., *Chimia,* 1996, 50, 168–176; Altmann et al., *Biochem. Soc. Trans.,* 1996, 24, 630–637; and Altmann et al., *Nucleosides Nucleotides,* 1997, 16, 917–926). Relative to DNA, they display improved RNA affinity and higher nuclease resistance. Chimeric oligonucleotides with 2-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

LNAs (oligonucleotides wherein the 2' and 4' positions are connected by a bridge) also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

LNAs in which the 2'-hydroxyl group is linked to the 4' carbon atom of the sugar ring thereby forming a 2'-C, 4'-C-oxymethylene linkage thereby forming a bicyclic sugar moiety. The linkage is preferably a methylene ($-CH_2-$)$_n$ group bridging the 2' oxygen atom and the 4' carbon atom wherein n is 1 or 2 (Singh et al., *Chem. Commun.,* 1998, 4, 455–456). LNA and LNA analogs display very high duplex thermal stabilities with complementary DNA and RNA (Tm=+3 to +10 C), stability towards 3'-exonucleolytic degradation and good solubility properties. Other preferred bridge groups include the 2'-$CH_2OCH_2$-4' bridge.

While the present invention is concerned primarily with oligonucleotides, some oligonucleotide mimetics may, with appropriate changes to the starting materials, also be prepared by processes according to the present invention. Oligonucleotide mimetics include compounds in which the oligonucleotide sugar has been replaced with a heterocyclic or carbocyclic ring structure. Such compounds are depicted in Formula 3, below.

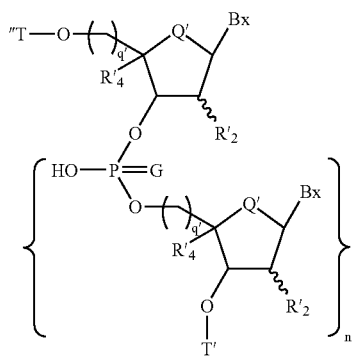

(3)

In Formula 3, G, Bx, n, $R'_2$ and $R'_4$ each have the meanings previously defined. The groups T' and T'' are each H, or conjugate groups, such as protecting groups and substituents. Each Q' is independently O, S, NR''', C(R''')$_2$, or $-CR'''=CR'''-$, where each R''' is H, alkyl, or where two R''' groups are on the same or adjacent carbon atoms, they may form a carbocyclic or heterocyclic ring, wherein the ring contains one or two of N, O or S. Preferred values of R''' are H and $C_1$–$C_4$ alkyl.

The foregoing oligonucleotides and oligonucleotide mimetics may be manufactured by any art-recognized method of forming phosphate diester or phosphorothioate diester linkages between successive nucleoside or nucleoside mimetic units. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioate and alkylated derivatives.

A preferred process of synthesizing oligomeric compounds utilizes phosphoramidite chemistry on a support media. The phosphoramidites can modified at the heterocyclic base, the sugar, or both positions to enable the synthesis of oligonucleotides and modified oligonucleotides.

Illustrative examples of the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, issued Jun. 29, 1993, and U.S. Pat. No. 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

The phosphoramidite method is as follows:

Phosphoramidites are prepared by reacting a suitable nucleoside or modified nucleoside (formula 4) with a phosphorodiamidite (formula 5) to form a phosphoramidite (formula 6).

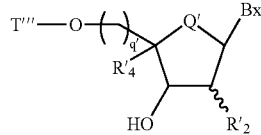
(4)

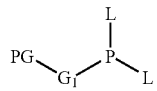
(5)

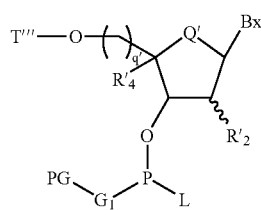
(6)

Each of the variables Q', Bx, R'$_2$, R'$_4$, and q' is as previously defined. L is an amine leaving group; PG is a phosphorus protecting group; G$_1$ is O or S; and T''' is a hydroxyl protecting group, each as more specifically defined herein.

A support-bound nucleoside of Formula 7 is first deprotected at the 5'-position (resulting in a free 5'-OH group), after which a first amidite is coupled to a support-bound nucleoside to form a support-bound dimer of Formula 8, which is then oxidized (e.g. sulfurized), and subjected to a capping step to form a support bound dimer of Formula 9.

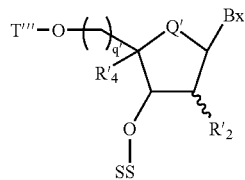
(7)

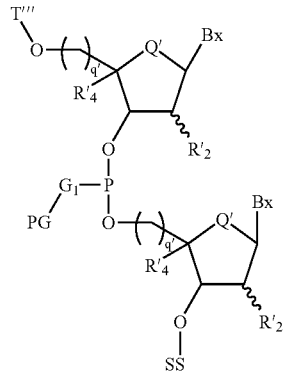
(8)

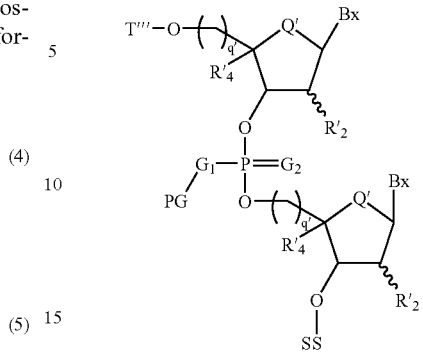
(9)

The 5'-deprotection, coupling, oxidation and capping steps are then repeated n-2 times to form a support-bound oligomer of Formula 10.

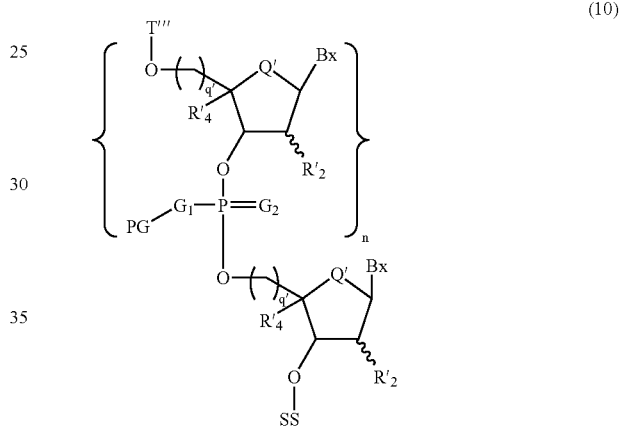
(10)

This compound is then cleaved from the solid support, 5'-deprotected, and purified to yield an oligomer of Formula 3, as described herein.

In each of the foregoing Formulae, SS represents a solid support, each PG is a phosphorus protecting group as defined herein, n is an integer, G$_1$ and G$_2$ are independently O or S, and each Bx, R'$_2$, R'$_4$, Q', and q' is independently as defined in Formula 3.

In addition to phosphate diester and phosphorothioate diester linkages, other linkers are known in the art. While the primary concern of the present invention has to do with phosphate diester and phosphorothioate diester oligonucleotides, chimeric compounds having more than one type of linkage, as well as oligomers having non-phosphate/phosphorothioate diester linkages as described in further detail below, are also contemplated in whole or in part within the context of the present invention.

Exemplary non-phosphate/phosphorothioate diester linkages contemplated within the skill of the art include: phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates. Additional linkages include: thiodiester (—O—C(O)—S—), thionocarbamate (—O—C(O)(NJ)—S—), siloxane (—O—Si(J)$_2$—O—), carbamate (—O—C(O)—NH— and —NH—C(O)—O—), sulfamate (—O—S(O)(O)—N— and —N—S(O)(O)—N—, morpholino sulfamide (—O—S(O)(N(morpholino)-), sulfonamide (—O—SO$_2$—NH—), sulfide (—CH$_2$—S—CH$_2$—), sulfonate (—O—SO$_2$—CH$_2$—), N,N'-dimethylhydrazine (—CH$_2$—N(CH$_3$)—N(CH$_3$)—), thioformacetal (—S—CH$_2$—O—), formacetal (—O—CH$_2$—O—), thioketal (—S—C(J)$_2$—O—), ketal (—O—C(J)$_2$—O—), amine (—NH—CH$_2$—CH$_2$), hydroxylamine (—CH$_2$—N(J)—O—), hydroxylimine (—CH=N—O—), and hydrazinyl (—CH$_2$—N(H)N(H)—).

In each of the foregoing substructures relating to internucleoside linkages, J denotes a substituent group that is commonly hydrogen or an alkyl group or a more complicated group that varies from one type of linkage to another.

In addition to linking groups as described above that involve the modification or substitution of the —O—P—O— atoms of a naturally occurring linkage, included within the scope of the present invention are linking groups that include modification of the 5'-methylene group as well as one or more of the —O—P—O— atoms. Linkages of this type are well documented in the prior art and include without limitation the following: amides (—CH$_2$—CH$_2$N(H)—C(O)) and —CH$_2$—O—N=CH—; and alkylphosphorus (—C(J)$_2$—P(=O)(OJ)—C(J)$_2$—C(J)$_2$—). J is as described above.

Synthetic schemes for the synthesis of the substitute internucleoside linkages described above are disclosed in: U.S. Pat. Nos. 5,466,677; 5,034,506; 5,124,047; 5,278,302; 5,321,131; 5,519,126; 4,469,863; 5,455,233; 5,214,134; 5,470,967; 5,434,257. Additional background information relating to internucleoside linkages can be found in: WO 91/08213; WO 90/15065; WO 91/15500; WO 92/20822; WO 92/20823; WO 91/15500; WO 89/12060; EP 216860; PCT/US 92/04294; PCT/US 90/03138; PCT/US 91/06855; PCT/US 92/03385; PCT/US 91/03680; U.S. application Ser. Nos. 07/990,848; 07/892,902; 07/806,710; 07/763,130; 07/690,786; Stirchak, E. P., et al., *Nucleic Acid Res.*, 1989, 17, 6129–6141; Hewitt, J. M., et al., 1992, 11, 1661–1666; Sood, A., et al., *J. Am. Chem. Soc.*, 1990, 112, 9000–9001; Vaseur, J. J. et al., *J. Am. Chem. Soc.*, 1992, 114, 4006–4007; Musichi, B., et al., *J. Org. Chem.*, 1990, 55, 4231–4233; Reynolds, R. C., et al., *J. Org. Chem.*, 1992, 57, 2983–2985; Mertes, M. P., et al., *J. Med. Chem.*, 1969, 12, 154–157; Mungall, W. S., et al., *J. Org. Chem.*, 1977, 42, 703–706; Stirchak, E. P., et al., *J. Org. Chem.*, 1987, 52, 4202–4206; Coull, J. M., et al., *Tet. Lett.*, 1987, 28, 745; and Wang, H., et al., *Tet. Lett.*, 1991, 32, 7385–7388.

Phosphoramidites used in the synthesis of oligonucleotides are available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). These commercial sources sell high purity phosphoramidites generally having a purity of better than 98%. Those not offering an across the board purity for all amidites sold will in most cases include an assay with each lot purchased giving at least the purity of the particular phosphoramidite purchased. Commercially available phosphoramidites are prepared for the most part for automated DNA synthesis and as such are prepared for immediate use for synthesizing desired sequences of oligonucleotides. Phosphoramidites may be prepared by methods disclosed by e.g. Caruthers et al. (U.S. Pat. Nos. 4,415,732; 4,458,066; 4,500,707; 4,668,777; 4,973,679; and 5,132,418) and Köster et al. (U.S. Pat. No. Re. 34,069).

Oligonucleotides are generally prepared, as described above, on a support medium, e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support media can be soluble or insoluble, or may possess variable solubility in different solvents to allow the growing support bound polymer to be either in or out of solution as desired. Traditional support media such as solid supports are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., *Chem. Rev.*, 1997, 97, 489–510).

The term support media is intended to include all forms of support known to the art skilled for the synthesis of oligomeric compounds and related compounds such as peptides. Some representative support media that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, *Angew. Chem. Internal. Ed.* 1972, 11, 314, sold under the trademark "PORASIL E" by Waters Associates, Framingham, Mass., USA); the mono ester of 1,4-dihydroxymethylbenzene and silica (see Bayer and Jung, *Tetrahedron Lett.*, 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225–231).

Further support media amenable to the present invention include without limitation PEPS support a polyethylene (PE) film with pendant long-chain polystyrene (PS) grafts (molecular weight on the order of $10^6$, (see Berg, et al., *J. Am. Chem. Soc.*, 1989, 111, 8024 and International Patent Application WO 90/02749),). The loading capacity of the film is as high as that of a beaded matrix with the additional flexibility to accommodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell plates have not indicated any limitations of the synthetic efficacy.

Further support media amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, *Bioorg. Chem.* 1979, 8, 351, and J. C. S. Perkin 1538 (1981)).

Further support media amenable to the present invention include without limitation a composite of a resin and another material that is also substantially inert to the organic synthesis reaction conditions employed. One exemplary composite (see Scott, et al., *J. Chrom. Sci.*, 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113–116). Contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA*, 1984, 81, 3998). A "tea bag" containing traditionally-used polymer beads. (Houghten, *Proc. Natl. Acad. Sci. USA*, 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175–178). Combining of reaction vessels via a manifold (Gorman, *Anal. Biochem.*, 1984, 136, 397). Multicolumn solid-phase synthesis (e.g., Krchnak, et al., *Int. J. Peptide Protein Res.*, 1989, 33, 209), and Holm and Meldal, in "Proceedings of the 20th European Peptide Symposium", G. Jung and E. Bayer, eds., Walter de Gruyter & Co., Berlin, 1989 pp. 208–210). Cellulose paper (Eichler, et al., *Collect. Czech. Chem. Commun.*, 1989, 54, 1746). Support mediated synthesis of peptides have also been reported (see, *Synthetic Peptides: A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and Re-34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Köster U.S. Pat. Nos. 4,725,677 and Re. 34,069.

Commercially available equipment routinely used for the support media based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

In general, the phosphorus protecting group (PG) is an alkyl group or a β-eliminable group having the formula —$CH_2CH_2$—$G_w$, wherein $G_w$ is an electron-withdrawing group. Suitable examples of PG that are amenable to use in connection with the present invention include those set forth in the Caruthers U.S. Pat. Nos. 4,415,732; 4,458,066; 4,500,707; 4,668,777; 4,973,679; and 5,132,418; and Köster U.S. Pat. Nos. 4,725,677 and Re. 34,069. In general the alkyl or cyanoethyl withdrawing groups are preferred, as commercially available phosphoramidites generally incorporate either the methyl or cyanoethyl phosphorus protecting group.

The method for removal of PGs depends upon the specific PG to be removed. The β-eliminable groups, such as those disclosed in the Köster et al. patents, are generally removed in a weak base solution, whereby an acidic β-hydrogen is extracted and the —$CH_2CH_2$—$G_w$ group is eliminated by rearrangement to form the corresponding acrylo-compound $CH_2$=CH—$G_w$. In contrast, an alkyl group is generally removed by nucleophilic attack on the α-carbon of the alkyl group. Such PGs are described in the Caruthers et al. patents, as cited herein.

Oxidizing reagents for making phosphate diester linkages under the phosphoramidite protocol have been described by e.g. Caruthers et al. and Köster et al., as cited herein. Oxidizing reagents for making phosphorothioate diester linkages include phenylacetyldisulfide (PADS), as described by Cole et al. in U.S. Pat. No. 6,242,591. In some embodiments of the invention, the phosphorothioate diester and phosphate diester linkages may be alternated between sugar subunits. In other embodiments of the present invention, phosphorothioate linkages alone may be employed.

Reagents for cleaving an oligonucleotide from a support are set forth, for example, in the Caruthers et al. and Köster et al. patents, as cited herein.

The oligonucleotide may be worked up by standard procedures known in the art, for example by size exclusion chromatography, high performance liquid chromatography (e.g. reverse-phase HPLC), differential precipitation, etc. In some embodiments according to the present invention, the oligonucleotide is cleaved from a solid support while the 5'-OH protecting group is still on the ultimate nucleoside. This so-called DMT-on (or trityl-on) oligonucleotide is then subjected to chromatography, after which the DMT group is removed by treatment in an organic acid, after which the oligonucleotide is de-salted and further purified to form a final product.

The 5'-hydroxylprotecting groups may be any groups that are selectively removed under suitable conditions. In particular, the 4,4'-dimethoxytriphenylmethyl (DMT) group is a favored group for protecting at the 5'-position, because it is readily cleaved under acidic conditions (e.g. in the presence of dichloroacetic acid (DCA), trichloroacetic acid (TCA), or acetic acid. Removal of DMT from the support-bound oligonucleotide is generally performed with DCA. Removal of oligonucleotide after cleavage from the support is generally performed with acetic acid.

As described herein, oligonucleotides can be prepared as chimeras with other oligomeric moieties. In the context of this invention, the term "oligomeric compound" refers to a polymeric structure capable of hybridizing a region of a nucleic acid molecule, and an "oligomeric moiety" a portion of such an oligomeric compound. Oligomeric compounds include oligonucleotides, oligonucleosides, oligonucleotide analogs, modified oligonucleotides and oligonucleotide mimetics. Oligomeric compounds can be linear or circular, and may include branching. They can be single stranded or double stranded, and when double stranded, may include overhangs. In general an oligomeric compound comprises a backbone of linked monomeric subunits where each linked monomeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras. As is known in the art, a nucleoside is a base-sugar combination. The base portion of the nucleoside is normally a heterocyclic base moiety. The two most common classes of such heterocyclic bases are purines and pyrimidines. In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In the context of this invention, the term "oligonucleotide mimetic" refers to an oligonucleotide wherein the backbone of the nucleotide units has been replaced with novel groups. Although the term is intended to include oligomeric compounds wherein only the furanose ring or both the furanose ring and the internucleotide linkage are replaced with novel groups, replacement of only the furanose ring is also referred to in the art as being a sugar surrogate. Oligonucleotide mimetics can be further modified to incorporate one or more modified heterocyclic base moieties to enhance properties such as hybridization.

One oligonucleotide mimetic that has been reported to have excellent hybridization properties, is peptide nucleic acids (PNA). The backbone in PNA compounds is two or more linked aminoethylglycine units that give PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

PNA has been modified to incorporate numerous modifications since the basic PNA structure was first prepared. The basic structure is shown below:

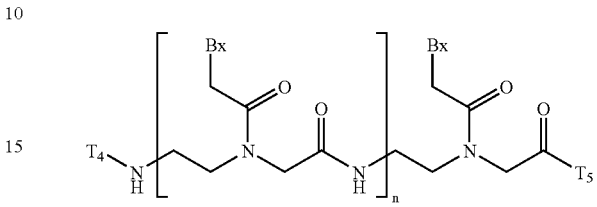

wherein

Bx is a heterocyclic base moiety;

$T_4$ is hydrogen, an amino protecting group, —C(O)R$_5$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, R$_5$, D or L α-amino acid linked via the α-amino group or optionally through the α-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$–$C_6$ alkyl, or an amino protecting group;

$Z_2$ is hydrogen, $C_1$–$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$–$C_6$ alkyl, —C(=O)—CH$_3$, benzyl, benzoyl, or —(CH$_2$)$_n$—N(H)$Z_1$;

each J is O, S or NH;

R$_5$ is a carbonyl protecting group; and n is from 2 to about 50.

Another class of oligonucleotide mimetic that has been studied is based on linked morpholino units (morpholino nucleic acids) having heterocyclic base moieties attached to the morpholino ring. There are a number of linking groups reported that are used to link the morpholino rings. A preferred class of linking groups was selected as being non-ionic. The non-ionic morpholino-based oligomeric compounds are less likely to have undesired interactions with cellular proteins (Dwaine A. Braasch and David R. Corey, Biochemistry, 2002, 41(14), 4503–4510). Morpholino-based oligomeric compounds are disclosed in U.S. Pat. No. 5,034,506, issued Jul. 23, 1991.

The morpholino class of oligomeric compounds has been prepared having a variety of different linking groups (L$_2$)

joining the monomeric subunits. The formula of the basic morpholino oligomeric compound is shown below:

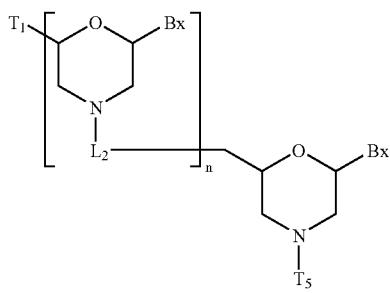

wherein
T$_1$ is hydroxyl or a protected hydroxyl;
T$_5$ is hydrogen or a phosphate or phosphate derivative;
L$_2$ is a linking group; and
n is from 2 to about 50.

Another class of oligonucleotide mimetic that has been studied is based on linked morpholino units having heterocyclic bases attached to the morpholino ring. Morpholino-based oligomeric compounds are non-ionic mimics of oligonucleotides, which are less likely to form undesired interactions with cellular proteins (Dwaine A. Braasch and David R. Corey, Biochemistry, 2002, 41(14), 4503–4510). Morpholino-based oligomeric compounds are disclosed in U.S. Pat. No. 5,034,506, issued Jul. 23, 1991.

The morpholino class of oligomeric compounds has been prepared having a variety of different linking groups joining the monomeric subunits. The formula of the basic morpholino oligomeric compound is shown below:

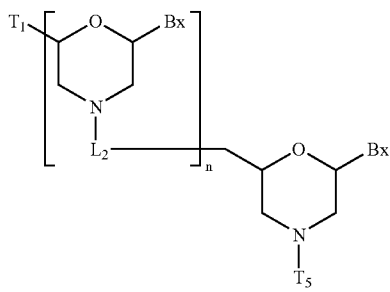

wherein
T$_1$ is hydroxyl or a protected hydroxyl;
T$_5$ is hydrogen or a phosphate or phosphate derivative;
L$_2$ is a linking group; and
n is from 2 to about 50.

A further class of oligonucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595–8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. Coli RNase resulting in cleavage of the target RNA strand.

The general formula of CeNA is shown below:

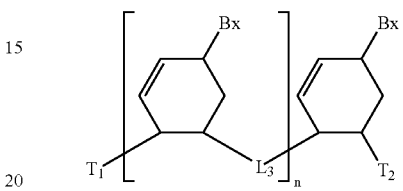

wherein
each Bx is a heterocyclic base moiety;
T$_1$ is hydroxyl or a protected hydroxyl; and
T$_2$ is hydroxyl or a protected hydroxyl.

Another class of oligonucleotide mimetic is referred to as phosphonomonoester nucleic acids, which in one aspect have a similarity to PNA but incorporate a phosphorus group in the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below along with one selection of Markush variables that give a compound having a resemblance to PNA.

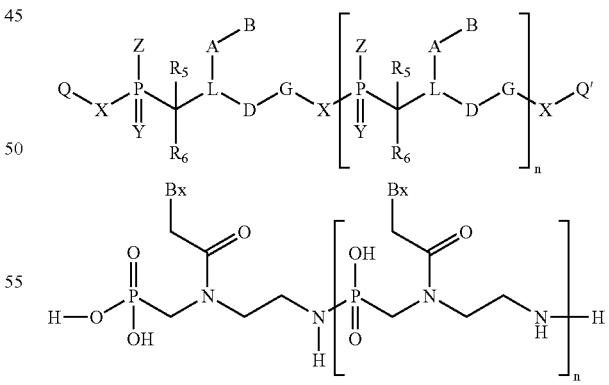

The term "nucleobase," as used herein, is intended to by synonymous with "nucleic acid base or mimetic thereof" as herein described. In general, a nucleobase is any substructure that contains one or more atoms or groups of atoms capable of hydrogen bonding to a base of an oligonucleotide. Thus, the term "nucleobase" encompasses naturally-occurring purines and pyrimidines (guanine, adenine, thymine, cytidine and uracil), as well as protected analogs thereof and a wide variety of mimetic moieties as described herein.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., *FEBS Lett.,* 1990, 259, 327; Svinarchuk et al., *Biochimie,* 1993, 75, 49), a phospholipid, e.g., dihexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241; 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned, and each of which is herein incorporated by reference.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

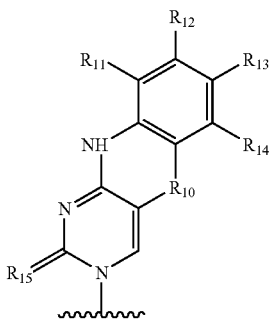

Representative cytosine analogs that make 3 hydrogen bonds with a guanosine in a second strand include 1,3-diazaphenoxazine-2-one ($R_{10}$=O, $R_{11}$–$R_{14}$=H) [Kurchavov, et al., *Nucleosides and Nucleotides*, 1997, 16, 1837–1846], 1,3-diazaphenothiazine-2-one ($R_{10}$=S, $R_{11}$–$R_{14}$=H), [Lin, K.-Y.; Jones, R. J.; Matteucci, M. *J. Am. Chem. Soc.* 1995, 117, 3873–3874] and 6,7,8,9-tetrafluoro-1,3-diazaphenoxazine-2-one ($R_{10}$=O, $R_{11}$–$R_{14}$=F) [Wang, J.; Lin, K.-Y., Matteucci, M. *Tetrahedron Lett.* 1998, 39, 8385–8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. Patent Application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—(CH$_2$)$_2$—NH$_2$, $R_{12-14}$=H) [Lin, K.-Y.; Matteucci, M. *J. Am. Chem. Soc.* 1998, 120, 8531–8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety. Such compounds include those having the formula:

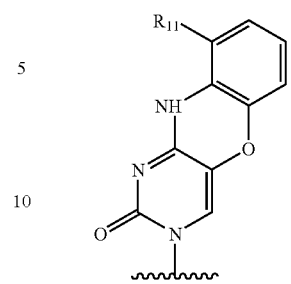

wherein $R_{11}$ includes (CH$_3$)$_2$N—(CH$_2$)$_2$—O—; H$_2$N—(CH$_2$)$_3$—; Ph-CH$_2$—O—C(=O)—N(H)—(CH$_2$)$_3$—; H$_2$N—; Fluorenyl-CH$_2$—O—C(=O)—N(H)—(CH$_2$)$_3$—; Phthalimidyl-CH$_2$—O—C(=O)—N(H)—(CH$_2$)$_3$—; Ph-CH$_2$—O—C(=O)—N(H)—(CH$_2$)$_2$—O—; Ph-CH$_2$—O—C(=O)—N(H)—(CH$_2$)$_3$—O—; (CH$_3$)$_2$N—N(H)—(CH$_2$)$_2$—O—; Fluorenyl-CH$_2$—O—C(=O)—N(H)—(CH$_2$)$_2$—O—; Fluorenyl-CH$_2$—O—C(=O)—N(H)—(CH$_2$)$_3$—O—; H$_2$N—(CH$_2$)$_2$—O—CH$_2$—; N$_3$—(CH$_2$)$_2$—O—CH$_2$—; H$_2$N—(CH$_2$)$_2$—O—, and NH$_2$C(=NH)NH—.

Also disclosed are tricyclic heterocyclic compounds of the formula:

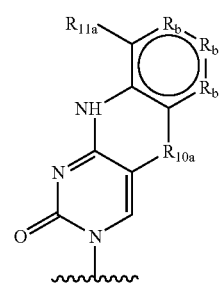

wherein $R_{10a}$ is O, S or N—CH$_3$;

$R_{11a}$ is A(Z)$_{x1}$, wherein A is a spacer and Z independently is a label bonding group bonding group optionally bonded to a detectable label, but $R_{11a}$ is not amine, protected amine, nitro or cyano;

$X_1$ is 1, 2 or 3; and $R_b$ is independently —CH=, —N=, —C(C$_{1-8}$ alkyl)— or —C(halogen)—, but no adjacent $R_b$ are both —N=, or two adjacent $R_b$ are taken together to form a ring having the structure:

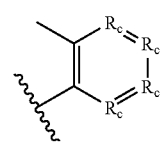

where $R_c$ is independently —CH=, —N=, —C(C$_{1-8}$ alkyl)— or —C(halogen)—, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNAse H, enhance cellular uptake and exhibit an increased antisense activity [Lin, K-Y; Matteucci, M. *J. Am. Chem. Soc.* 1998, 120, 8531–8532]. The activity enhancement was even more pronounced in case of G-clamp, as a single substitution was shown to significantly improve the in vitro potency of a 20 mer 2'-deoxyphosphorothioate oligonucleotides [Flanagan, W. M.; Wolf, J. J.; Olson, P.; Grant, D.; Lin, K.-Y.; Wagner, R. W.; Matteucci, M. *Proc. Natl. Acad. Sci. USA,* 1999, 96, 3513–3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

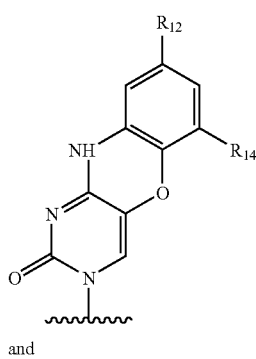

and

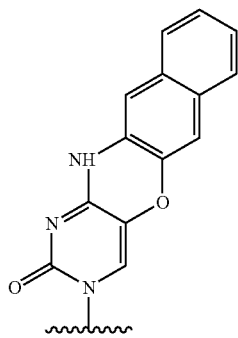

wherein $R_{14}$ is $NO_2$ or both $R_{14}$ and $R_{12}$ are independently —$CH_3$. The synthesis of these compounds is disclosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997, the contents of which are commonly assigned with this application and are incorporated herein in their entirety.

Further tricyclic heterocyclic compounds amenable to the present invention also disclosed in the "257, 177 and 269" patents include those having the formula:

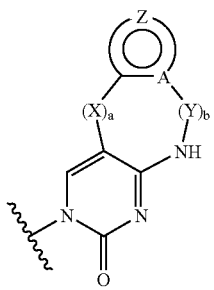

a and b are independently 0 or 1 with the total of a and b being 0 or 1;

A is N, C or CH;

X is S, O, C=O, NH or $NCH_2$, $R^6$;

Y is C=O;

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 non-bridging ring carbon atom is substituted with $R^{20}$ or =O;

or Z is taken together with A to form an aryl ring structure comprising 6 ring atoms wherein the aryl ring carbon atoms are unsubstituted with other than H or at least 1 nonbridging ring carbon atom is substituted with $R^6$ or O;

$R^6$ is independently H, $C_{1-6}$ alkyl, $C_{2-6}$ alkenyl, $C_{2-6}$ alkynyl, $NO_2$, $N(R^3)_2$, CN or halo, or an $R^6$ is taken together with an adjacent Z group $R^6$ to complete a phenyl ring;

$R^{20}$ is, independently, H, $C_{1-6}$ alkyl, $C_{2-6}$ alkyl, $C_{2-6}$ alkenyl, $C_{2-6}$ alkynyl, $NO_2$, $N(R^{21})_2$, CN, or halo, or an $R^{20}$ is taken together with an adjacent $R^{20}$ to complete a ring containing 5 or 6 ring atoms, and tautomers, solvates and salts thereof;

$R^{21}$ is, independently, H or a protecting group;

$R^3$ is a protecting group or H; and tautomers, solvates and salts thereof.

More specific examples included in the "257, 177 and 269" Patents are compounds of the formula:

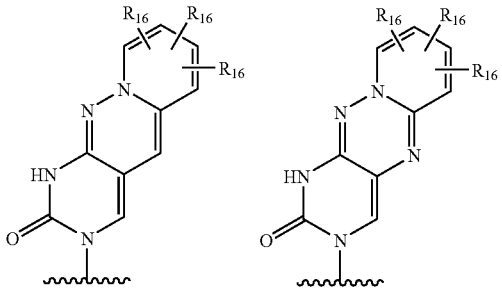

-continued

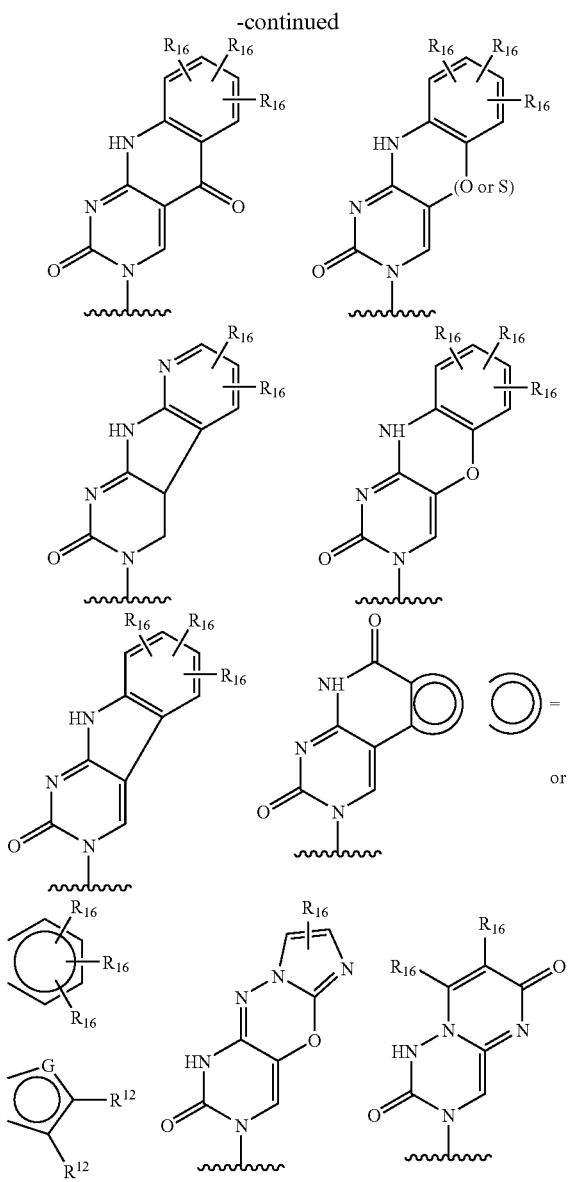

wherein each $R_{16}$, is, independently, selected from hydrogen and various substituent groups.

Further polycyclic base moieties having the formula:

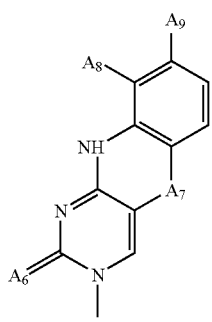

wherein:
$A_6$ is O or S;

$A_7$ is $CH_2$, N—$CH_3$, O or S;
each $A_8$ and $A_9$ is hydrogen or one of $A_8$ and $A_9$ is hydrogen and the other of $A_8$ and $A_9$ is selected from the group consisting of:

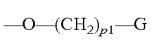

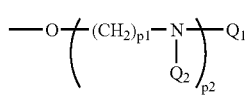

and
wherein:
G is —CN, —$OA_{10}$, —$SA_{10}$, —N(H)$A_{10}$, —ON(H)$A_{10}$ or —C(=NH)N(H)$A_{10}$;
$Q_1$ is H, —NH$A_{10}$, —C(=O)N(H)$A_{10}$, —C(=S)N(H)$A_{10}$ or —C(=NH)N(H)$A_{10}$;
each $Q_2$ is, independently, H or Pg;
$A_{10}$ is H, Pg, substituted or unsubstituted $C_1$-$C_{10}$ alkyl, acetyl, benzyl,
—$(CH_2)_{p3}NH_2$, —$(CH_2)_{p3}N(H)Pg$, a D or L α-amino acid, or a peptide derived from D, L or racemic α-amino acids;
Pg is a nitrogen, oxygen or thiol protecting group;
each p1 is, independently, from 2 to about 6;
p2 is from 1 to about 3; and
p3 is from 1 to about 4;
are disclosed in Unites States patent application Ser. No. 09/996,292 filed Nov. 28, 2001, which is commonly owned with the instant application, and is herein incorporated by reference.

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.,* 2000, 480, 17–24; Celis, et al., *FEBS Lett.,* 2000, 480, 2–16), SAGE (serial analysis of gene expression) (Madden, et al., *Drug Discov. Today,* 2000, 5, 415–425), READS (restriction enzyme amplification of digested cDNAs) (Prashar and Weissman, *Methods Enzymol.,* 1999, 303, 258–72), TOGA (total gene expression analysis) (Sutcliffe, et al., *Proc. Natl. Acad. Sci. U.S.A.,* 2000, 97, 1976–81), protein arrays and proteomics (Celis, et al., *FEBS Lett.,* 2000, 480, 2–16; Jungblut, et al., *Electrophoresis,* 1999, 20, 2100–10), expressed sequence tag (EST) sequencing (Celis, et al., *FEBS Lett.,* 2000, 480, 2–16; Larsson, et al., *J. Biotechnol.,* 2000, 80, 143–57), subtractive RNA fingerprinting (SuRF) (Fuchs, et al., *Anal. Biochem.,* 2000, 286, 91–98; Larson, et al., *Cytometry,* 2000, 41, 203–208), subtractive cloning, differential display (DD) (Jurecic and Belmont, *Curr. Opin. Microbiol.,* 2000, 3, 316–21), comparative genomic hybridization (Carulli, et al., *J. Cell Biochem. Suppl.,* 1998, 31, 286–96), FISH (fluorescent in situ hybridization) techniques (Going and Gusterson, *Eur. J. Cancer,* 1999, 35, 1895–904) and mass spectrometry methods (reviewed in To, *Comb. Chem. High Throughput Screen,* 2000, 3, 235–41).

The specificity and sensitivity of antisense are also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway.

It is thus established that oligonucleotides can be useful therapeutic modalities that can be configured to be useful in treatment regimes for treatment of cells, tissues and animals, especially humans.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a particular protein. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a particular protein, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. mRNA transcripts produced via the process of splicing of two (or more) mRNAs from different gene sources are known as "fusion transcripts". It has also been found that introns can be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable.

An antisense compound is specifically hybridizable when binding of the compound to the target DNA or RNA molecule interferes with the normal function of the target DNA or RNA to cause a loss of activity, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. It is preferred that the antisense compounds of the present invention comprise at least 80% sequence complementarity with the target nucleic acid, more that they comprise 90% sequence complementarity and even more comprise 95% sequence complementarity with the target nucleic acid sequence to which they are targeted. Percent complementarity of an antisense compound with a target nucleic acid can be determined routinely using basic local alignment search tools (BLAST programs) (Altschul et al., *J. Mol. Biol.*, 1990, 215, 403–410; Zhang and Madden, *Genome Res.*, 1997, 7, 649–656).

Antisense and other compounds of the invention, which hybridize to the target and inhibit expression of the target, are identified through experimentation, and representative sequences of these compounds are hereinbelow identified as preferred embodiments of the invention. The sites to which these preferred antisense compounds are specifically hybridizable are hereinbelow referred to as "preferred target regions" and are therefore preferred sites for targeting. As used herein the term "preferred target region" is defined as at least an 8-nucleobase portion of a target region to which an active antisense compound is targeted. While not wishing to be bound by theory, it is presently believed that these target regions represent regions of the target nucleic acid that are accessible for hybridization.

While the specific sequences of particular preferred target regions are set forth below, one of skill in the art will recognize that these serve to illustrate and describe particular embodiments within the scope of the present invention. Additional preferred target regions may be identified by one having ordinary skill.

Target regions 8–80 nucleobases in length comprising a stretch of at least eight (8) consecutive nucleobases selected from within the illustrative preferred target regions are considered to be suitable preferred target regions as well.

Exemplary good preferred target regions include DNA or RNA sequences that comprise at least the 8 consecutive nucleobases from the 5'-terminus of one of the illustrative preferred target regions (the remaining nucleobases being a consecutive stretch of the same DNA or RNA beginning immediately upstream of the 5'-terminus of the target region and continuing until the DNA or RNA contains about 8 to about 80 nucleobases). Similarly good preferred target regions are represented by DNA or RNA sequences that comprise at least the 8 consecutive nucleobases from the 3'-terminus of one of the illustrative preferred target regions (the remaining nucleobases being a consecutive stretch of the same DNA or RNA beginning immediately downstream of the 3'-terminus of the target region and continuing until the DNA or RNA contains about 8 to about 80 nucleobases). One having skill in the art, once armed with the empirically-derived preferred target regions illustrated herein will be able, without undue experimentation, to identify further preferred target regions. In addition, one having ordinary skill in the art will also be able to identify additional compounds, including oligonucleotide probes and primers, that specifically hybridize to these preferred target regions using techniques available to the ordinary practitioner in the art.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands. The structure-stability relationships of a large number of nucleic acid modifications have been reviewed (Freier and Altmann, *Nucl. Acids Research*, 1997, 25, 4429–4443).

EXAMPLES

The present invention may be further appreciated upon reference to the following, non-limiting examples.

1. [5'-O-(4,4'-Dimethoxytriphenylmethyl)-2'-O-(2-methoxyethyl)-N⁶-benzoyladenosin-3'-O-yl]-2-cyanoethl-N,N-diisopropylphosphoramidite 5'-O-(4,4'-Dimethoxytriphenymethyl)-2'-O-(2-methoxyethyl)-N⁶-benzoyladenosine (1098 g, 1.5 mol) was dissolved in anhydrous DMF (3 L). The solution was co-evaporated with toluene (300 ml) at 50° C. under reduced pressure. The mixture was cooled to room temperature and 2-cyanoethyl tetraisopropylphosphorodiamidite (680 g, 2.26 mol) and tetrazole (78.8 g, 1.24 mol) were added. The mixture was shaken until all tetrazole was dissolved and N-methylimidazole (30 ml) was added. The mixture was left at room temperature for 5 hours. Triethylamine (300 ml) was added. The mixture was diluted with DMF (1 L) and water (400 ml) and extracted with hexanes (3×3 L). The mixture was diluted with water (1.4 L) and extracted with the mixture of toluene (9 L) and hexanes (6 L). The two layers were separated and the upper layer was washed with DMF-water (60:40, v/v, 3×3 L) and water (3×2 L). The upper layer was dried ($Na_2SO_4$), filtered and evaporated to a sticky foam. The residue was co-evaporated with acetonitrile (2.5 L) under reduced pressure and dried to a constant weight (25° C./0.1 mmHg/40 h) to give the product as an off-white foam solid (1350 g, yield 96%).

2. [5'-O-(4,4'-Dimethoxytriphenylmethyl)-2'-O-(2-methoxyethyl)-N⁴-benzoyl-5-methylcytidin -3'-O-yl]-2-cyanoethyl-N,N-diisopropylphosphoramidite 5'-O-(4,4'-Dimethoxytriphenylmethyl)-2'-O-(2-methoxyethl)-N⁴-benzoyl-5-methylcytidine (1082 g, 1.5 mol) was dissolved in anhydrous dimethylformamide (DMF, 2L). The solution was co-evaporated with toluene (300 ml) at 50° C. under reduced pressure. The mixture was cooled to room temperature and 2-cyanoethyltetraisopropylphosphorodiamidite (680 g, 2.26 mol) and tetrazole (52.5 g, 0.75 mol) were added. The mixture was shaken until all tetrazole was dissolved and N-methylimidazole (30 ml) was added. The mixture was left at room temperature for 5 hours. Triethylamine (300 ml) was added. The mixture was diluted with DMF (1 L) and water (400 ml) and extracted with hexane (3×3 L). The mixture was diluted with water (1.2 L) and extracted with mixture of toluene (9 L) and hexanes (6 L). The two layers were separated and the upper layer was washed with DMF-water (60:40 v/v, 3×3 L) and water (3×2 L). The upper layer was dried ($Na_2SO_4$), filtered and evaporated. The residue was co-evaporated with acetonitrile (2×2 L) under reduced pressure and dried to a constant weight (25° C./0.1 mmHg/40 h) to give the product as an off-white foam solid (1336 g, yield 97%).

3. [5'-O-(4,4'-Dimethoxytripheylmethyl)-2'-O-(2-methoxyethyl)-N⁴-isobutyrylguanosin-3'-O-yl]-2-cyanoethyl-N,N-diisopropylphosphoramidite 5'-O-(4,4'-Dimethoxytriphenylmethyl)-2'-O-(2-methoxyethyl)-N⁴-isobutyryl guanosine (1426 g, 2.0 mol) was dissolved in anhydrous DMF (2L). The solution was co-evaporated with toluene (200 ml) at 50° C. under reduced pressure. The mixture was cooled to room temperature and 2-cyanoethyl tetraisopropylphosphorodiamidite (900 g, 3.0 mol) and tetrazole (68 g, 0.97 mol) were added. The mixture was shaken until all tetrazole was dissolved and N-methylimidazole (30 ml) was added. The mixture was left at room temperature for 5 hours. Triethylamine (300 ml) was added. The mixture was diluted with DMF (2 L) and water (600 ml) and extracted with hexanes (3×3 L). The mixture was diluted with water (2 L) and extracted with the mixture of toluene (10 L) and hexanes (5 L). The two layers were separated and the upper layer was washed with DMF-water (60:40, v/v, 3×3 L). Ethyl acetate (4 L) was added and the solution was washed with water (3×4 L). The upper layer was dried-($Na_2SO_4$), filtered and evaporated to about 4 kg. Hexane (4 L) was added and the mixture was mixed on a rotavaporator for 10 minutes. The supernatant liquid was decanted. The residue was co-evaporated with acetonitrile (2×2 L) under reduced pressure and dried to a constant weight (25° C./0.1 mm Hg/40 h) to give the product as an off-white foam solid (1660 g, yield: 91%).

4. [5'-O-(4,4'-Dimethoxytripheylmethyl)-2'-O-(2-methoxyethyl)-5-methyluridin-3'-O-yl]-2-cyanoethyl-N,N-diisopropylphosphoramidite 5'-O-(4,4'-Dimethoxytriphenylmethyl)-2'-O-(2-methoxyethyl)-5-methyluridine (1237 g, 2.0 mol) was dissolved in anhydrous DMF (2.5 L). The solution was co-evaporated with toluene (200 ml) at 50° C. under reduced pressure. The mixture was cooled to room temperature and 2-cyanoethyl tetraisopropylphosphorodiamidite (900 g, 3.0 mol) and tetrazole (70 g, 1.0 mol) were added. The mixture was shaken until all tetrazole was dissolved and N-methylimidazole (20 ml) was added. The mixture was left at room temperature for 5 hours. Triethylamine (300 ml) was added. The mixture was diluted with DMF (3.5 L) and water (600 ml) and extracted with hexane (3×3 L). The mixture was diluted with water (41.6 L) and extracted with the mixture of toluene (12 L) and hexanes (9 L). The two layers were separated and the upper layer was washed with DMF-water (7:3 v/v 3×3 L) and water (3×3 L). The upper layer was dried ($Na_2SO_4$), filtered, and evaporated. The residue was co-evaporated with acetonitrile (2×2 L) under reduced pressure and dried to a constant weight (25° C./0.1 mm Hg/40 h) to give the product as an off-white foam solid (1562 g, yield 95%).

5. Alternative Synthesis and Purification Procedures

The synthesis and purification of phosphoramidites have been demonstrated in acetonitrile according to the following general description. The amidite reaction (phos reagent+ PNS→amidite) was carried out in acetonitrile at a concentration of about 10 g PNS in 50 ml, using NMI triflate (about 0.5 equivalents) as activator and about 1.5 equivalents of phos reagent (2-cyanoethyl tetraisopropylphosphorodiamidite). Under these conditions, the reaction was generally complete within about 2 hr. The reaction was then quenched with TEA (6 ml) and water (10 ml), and was washed with an apolar phase, such as hexanes. The reaction mixture was then diluted with isopropyl ether (150 ml) and then washed with water (40 ml). (Upon addition of ether, some acetonitrile partitions into the ether phase. After the additional water is introduced, however, acetonitrile tends to partition back into the ether phase. The amidite product, being more hydrophobic than the water/acetonitrile phase, partitions into the ether phase.) It was noted that water/acetonitrile and isopropyl ether demonstrated improved (i.e. reduced) P(V) impurities as compared to the DMF/water and toluene procedure described herein. After separating the ether layer from the acetonitrile/water layer, it was then washed with 3 additional aliquots of 50 ml of water, which effectively removed acetonitrile remaining in the ether. The crude amidite product was of fair quality. The amidite was then subjected to one or more gumming out steps, as described herein. The resulting product was of good quality.

The person having skill in the art will recognize that further embodiments are possible within the general scope of the foregoing description and claims, and it would be within the skill of such skilled person to practice the invention as generally described herein.

All references cited herein are expressly incorporated herein by reference.

We claim:

1. A process of purifying a phosphitylated compound of formula I:

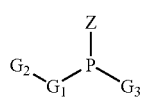

wherein $G_1$ is O or S;
$G_2$ is a protecting group;
$G_3$ is an amine;
Z is $Z_1$ or $Z_2$;
$Z_1$ has the formula:

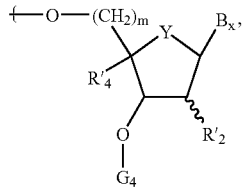

$Z_2$ has the formula:

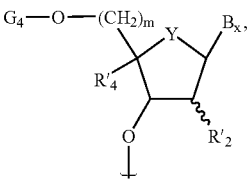

Y is O or S;
$R'_2$ is protected $OH$,; H, HO, $OR_5$, $NR_5R_6$, F, Cl, Br, alkyl, substituted alkyl, heterocyclyoalkyl, substituted heterocycloalkyl, aryl, substituted aryl, heteroaryl, substituted heteroaryl, aralkyl, substituted aralkyl, heterocycloaralkyl, substituted heterocycloaralkyl; or $R'_2$ and $R'_4$ together form a bridge;
each of $R_5$ and $R_6$ is independently alkyl, heterocycloalkyl, substituted heterocycloalkyl, aryl, substituted aryl, aralkyl, substituted aralkyl, hetaryl, substituted hetaryl, hetarylalkyl, substituted hetarylalkyl, alkenyl, substituted alkenyl, alkynyl, substituted alkynyl, alkanoyl, substituted alkanoyl, trialkylsilyl or substituted trialkylsilyl; or
when $R_5$ and $R_6$ are on the same nitrogen, $R_5$ and $R_6$ may be taken together with the nitrogen to which they are bound to form a heterocyclyl ring or a substituted heterocyclyl ring
$R'_4$ is H or together with $R'_2$ forms a bridge;
m is an integer of 0 or 1, $B_x$ is a heterocycle and $G_4$ is a hydroxy protecting group; the process comprising:
(a) providing the compound of formula I in a polar phase comprising a polar organic solvent and at least one impurity;
(b) adding a basic compound and a first portion of water to the polar phase;
(c) contacting the polar phase with a first apolar organic phase;
(d) separating the first apolar organic phase from the polar phase;
(e) adding a second portion of water to the polar phase and contacting the polar phase with a second apolar organic phase, the polar phase and the second apolar phase being contacted for a time sufficient for the compound of formula I to partition into the second apolar organic phase; and
(f) separating the second apolar phase from the polar phase.

2. The process of claim 1, wherein step (e) comprises substeps carried out in order:
(1) adding the second portion of water to the polar phase; and (2) contacting the polar phase with a second apolar organic phase.

3. The process of claim 2, wherein the second apolar phase comprises toluene.

4. The process of claim 2, wherein the polar phase comprises dimethylformamide.

5. The process of claim 1, wherein the step (e) is carried out in the order:
(1) contacting the polar phase with a second apolar organic phase; and
(2) adding the second portion of water to the polar phase.

6. The process of claim 5, wherein the second apolar phase comprises isopropyl ether or t-butyl methyl ether.

7. The process of claim 5, wherein the polar phase comprises acetonitrile.

8. The process according to claim 1, wherein $B_x$ is a nucleobase.

9. The process according to claim 1, wherein the basic compound in step (b) is an amine.

10. The process according to claim 1, wherein the basic compound in step (b) is a tertiary amine.

11. The process according to claim 1, wherein the basic compound in step (b) is triethyl amine.

12. The process according to claim 1,
wherein $G_3$ is NR'R",
wherein R' and R" are independently H or an organic moiety, or are taken together with the nitrogen to which they are attached to form a saturated or unsaturated heterocyclyl ring.

13. The process according to claim 12,
wherein R' and R" are independently H, alkyl, heterocycloalkyl, substituted heterocycloalkyl, aryl, substituted aryl, aralkyl, substituted aralkyl, hetaryl, substituted hetaryl, hetarylalkyl, substituted hetarylalkyl, alkenyl, substituted alkenyl, alkynyl, substituted alkynyl, alkanoyl, substituted alkanoyl, trialkylsilyl or substituted trialkylsilyl; or
R' and R" are taken together with the nitrogen to which they are attached to form a 4-8-membered, saturated heterocyclyl group, which is optionally further substituted; or
R' and R" are taken together with the nitrogen to which they are attached to form a 4-8-membered, unsaturated heterocyclyl group, which is optionally further substituted.

14. The process according to claim 1, wherein $G_2$ is substituted alkyl.

15. The process according to claim 14, wherein $G_2$ is substituted ethyl.

16. The process according to claim 15, wherein $G_2$ is cyanoethyl.

17. The process according to claim 1, wherein $G_4$ is dimethoxytrityl (DMT).

18. The process according to claim 1, wherein $G_1$ is O.

19. The process according to claim 1, wherein Z is $Z_1$.

20. The process according to claim 19, wherein m is 1.

21. The process according to claim 1, wherein Z is $Z_2$.

22. The process according to claim 21, wherein m is 1.

23. The process according to claim 1, wherein Z is $Z_1$ and $R'_2$ and $R'_4$ together form a bridge of subformula $R'_2$—O$(CH_2)_r$—$R'_4$, wherein r is 1 or 2, or $R'_2$—$CH_2OCH_2$—$R'_4$.

24. The process according to claim 23, wherein m is 1.

25. The process according to claim 23, wherein Z is $Z_2$ and $R'_2$ and $R'_4$ together form a bridge of subformula $R'_2$—O$(CH_2)_r$—$R'_4$, wherein r is 1 or 2, or $R'_2$—$CH_2OCH_2$—$R'_4$.

26. A process of purifying a phosphitylated compound of formula I:

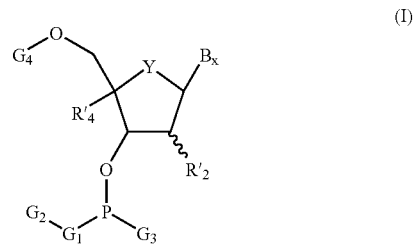

wherein $B_x$ is a heterocycle;

Y is O or S;

$R'_2$ is protected OH, H, OH, $OR_5$, $NR_5R_6$, F, Cl, Br, alkyl, substituted alkyl, heterocyclyoalkyl, substituted heterocycloalkyl, aryl, substituted aryl, heteroaryl, substituted heteroaryl, aralkyl, substituted aralkyl, heterocycloaralkyl, substituted heterocycloaralkyl; or $R'_2$ and $R'_4$ together form a bridge;

each of $R_5$ and $R_6$ is independently alkyl, heterocycloalkyl, substituted heterocycloalkyl, aryl, substituted aryl, aralkyl, substituted aralkyl, hetaryl, substituted hetaryl, hetarylalkyl, substituted hetarylalkyl, alkenyl, substituted alkenyl, alkynyl, substituted alkynyl, alkanoyl, substituted alkanoyl, trialkylsilyl or substituted trialkylsilyl; or when $R_5$ and $R_6$ are on the same nitrogen, $R_5$ and $R_6$ may be taken together with the nitrogen to which they are bound to form a heterocyclyl ring or a substituted heterocyclyl ring and $R'_4$ is H; or $R'_2$ and $R'_4$ together form a bridge;

$G_1$ is O or S;

$G_2$ is a protecting group;

$G_3$ is an amine; and $G_4$ is a protecting group;

the process comprising:
(a) providing the compound of formula I in a polar phase comprising a polar organic solvent and at least one impurity;
(b) adding a basic compound and water to the polar phase;
(c) contacting the polar phase with a first apolar organic phase;
(d) separating the first apolar organic phase from the polar phase;
(e) adding a second portion of water to the polar phase and contacting the polar phase with a second apolar organic phase, the polar phase and the second apolar phase being contacted for a time sufficient for the compound of formula I to partition into the second apolar organic phase; and
(f) separating the second apolar phase from the polar phase.

27. The process of claim 26, wherein step (e) comprises, in order, substeps:
(1) adding the second portion of water to the polar phase; and
(2) contacting the polar phase with a second apolar organic phase.

28. The process of claim 27, wherein polar phase comprises dimethylformamide.

29. The process of claim 27, wherein the second apolar organic phase comprises toluene.

30. The process of claim 26, wherein the step (e) comprises, in order, substeps:
(1) contacting the polar phase with a second apolar organic phase; and
(2) adding the second portion of water to the polar phase.

31. The process of claim 30, wherein the polar phase comprises acetonitrile.

32. The process of claim 30, wherein the second apolar organic phase comprises isopropyl ether or t-butyl methyl ether.

33. The process according to claim 26, wherein $B_x$ is a nucleobase.

34. The process according to claim 26, wherein $R'_2$ is OH, protected OH or a 2'-substituent, and $R'_2$ is in the ribo-conformation.

35. The process according to claim 26, wherein the basic compound in step (b) is an amine.

36. The process according to claim 26, wherein the basic compound in step (b) is a tertiary amine.

37. The process according to claim 26, wherein the basic compound in step (b) is triethyl amine.

38. The process according to claim 26,
wherein $G_3$ is NR'R",
wherein R' and R" are independently H or an organic radical, or are taken together with the nitrogen to which they are attached to form a saturated or unsaturated heterocyclyl ring.

39. The process according to claim 38,
wherein R' and R" are independently H, alkyl, heterocycloalkyl, substituted heterocycloalkyl, aryl, substituted aryl, aralkyl, substituted aralkyl, hetaryl, substituted hetaryl, hetarylalkyl, substituted hetarylalkyl, alkenyl, substituted alkenyl, alkynyl, substituted alkynyl, alkanoyl, substituted alkanoyl, trialkylsilyl or substituted trialkylsilyl; or
R' and R" are taken together with the nitrogen to which they are attached to form a 4-8-membered, saturated heterocyclyl group, which is optionally further substituted; or
R' and R" are taken together with the nitrogen to which they are attached to form a 4-8-membered, unsaturated heterocyclyl group, which is optionally thither substituted.

40. The process according to claim 26, wherein $G_2$ is substituted alkyl.

41. The process according to claim 40, wherein $G_2$ is substituted ethyl.

42. The process according to claim 41, wherein $G_2$ is cyanoethyl.

43. The process according to claim 26, wherein $G_4$ is DMT.

44. The process according to claim 26, wherein $G_1$ is O.

45. A process of purifying a phosphitylated compound of formula I:

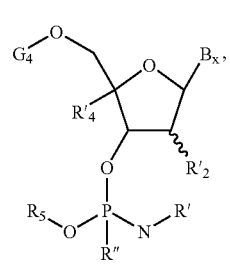

(I)

wherein $G_4$ is a protecting group; $B_x$ is a nucleobase;
R' and R" each independently represent a substituted- or unsubstituted hydrocarbyl radical having 1 to 10 carbon atoms, or taken together R' and R", together with the nitrogen to which they are attached, form a nitrogen-containing heterocyclyl ring, which optionally contains one or two additional hetero atoms, said nitrogen-containing heterocyclyl ring being saturated or unsaturated;
$R'_2$ is protected OH, H, OH, $OR_5$, $NR_5R_6$, F, Cl, Br, alkyl, substituted alkyl, heterocyclyoalkyl, substituted heterocycloalkyl, aryl, substituted aryl, heteroaryl, substituted heteroaryl, aralkyl, substituted aralkyl, heterocloaralkyl, substituted heterocycloaralkyl; or
$R'_2$ and $R'_4$ together form a bridge;
each of $R_5$ and R6 is independently alkyl, heterocycloalkyl, substituted heterocycloalkyl, aryl, substituted aryl, aralkyl, substituted aralkyl, hetaryl, substituted hetaryl, hetarylalkyl, substituted hetarylalkyl, alkenyl, substituted alkenyl, alkynyl, substituted alkynyl, alkanoyl, substituted alkanoyl, trialkylsilyl or substituted trialkylsilyl; or
when $R_5$ and $R_6$ are on the same nitrogen, $R_5$ and $R_6$ may be taken together with the nitrogen to which they are bound to form a heterocyclyl ring or a substituted heterocyclyl ring
$R'_4$ is H or together with $R'_2$ forms a bridge; and
$R_5$ represents a protecting group;
the process comprising:
(a) providing the compound of formula I in a polar solution comprising a polar organic solvent;
(b) adding a basic compound and a first portion of water to the polar solution;
(c) contacting the polar phase with a first apolar organic phase;
(d) removing the first apolar organic solvent from the polar phase;
(e) adding a second portion of water to the polar phase and contacting the polar phase with a second apolar organic phase, said polar phase and said apolar organic phase remaining in contact for a period sufficient to extract the compound of formula I into the second apolar organic phase; and
(f) separating the second apolar organic phase from the polar phase.

46. The process of claim 45, wherein step (e) comprises, in order, substeps:
(1) adding a second portion of water to the polar phase; and (2) contacting the polar phase with a second apolar organic phase.

47. The process according to claim 46, wherein the polar phase comprises dimethylformamide.

48. The process according to claim 46, wherein the second apolar organic phase comprises toluene.

49. The process of claim 45, wherein step (e) comprises, in order, substeps:
   (1) contacting the polar phase with a second apolar organic phase; and
   (2) adding a second portion of water to the polar phase.

50. The process of claim 49, wherein the second apolar organic phase comprises isopropyl ether or t-butyl methyl ether.

51. The process of claim 49, wherein the polar phase comprises acetonitrile.

52. The process according to claim 45, wherein $G_4$ is DMT.

53. The process according to claim 45, wherein $R'_2$ is H, methoxy or methoxyethoxy.

54. The process according to claim 45, wherein $R'_2$ is methoxyethoxy.

55. The process according to claim 45, wherein $B_x$ is an optionally protected nucleobase.

56. The process according to claim 45, wherein $B_x$ is optionally protected adenosinyl, cytidinyl, guanosinyl, 5-methyluridinyl, uridinyl, 5-methylcytidinyl.

57. The process according to claim 56, wherein $B_x$ is $N^6$-benzoyladenosinyl, $N^4$-benzoyl-5-methyl-cytidinyl, $N^4$-isobutyrylguanosinyl or 5-methyluridinyl.

58. The process according to claim 45, wherein $G_4$ is DMT; $R'_2$ is H, methoxyethoxy or methoxy; and $B_x$ is $N^6$-benzoyladenosinyl, $N^4$-benzoyl-5-methyl-cytidinyl, $N^4$-isobutyrylguanosinyl or 5-methyluridinyl.

59. The process according to claim 45, wherein the first apolar organic solvent comprises alkanes or aryl hydrocarbons.

60. The process according to claim 59, wherein the first apolar organic solvent comprises hexanes, heptane, cyclohexane or methycyclohexane.

61. The process according to claim 59, wherein the first apolar organic solvent comprises hexanes.

62. The process according to claim 45, wherein the polar solvent comprises acetonitrile, N,N-dimethylformamide or dichloromethane.

63. The process according to claim 62, wherein the polar solvent comprises N,N-dimethylformamide.

64. The process according to claim 45, wherein the basic compound of step (b) is an amine.

65. The process according to claim 64, wherein the basic compound of step (b) is a tertiary amine.

66. The process according to claim 65, wherein the basic compound of step (b) is triethyl amine.

67. The process according to claim 45, wherein the second apolar organic solvent comprises a mixture of saturated alkanes and aryl hydrocarbons.

68. The process according to claim 67, wherein the second apolar organic solvent comprises a mixture of hexanes and toluene.

69. A process of purifying a phosphoramidite by reverse precipitation at room temperature, said process comprising:
   (a) combining an intermediate purity phosphoramidite with a volume of an alkylated benzene solvent to form an organic solution;
   (b) gradually adding to the organic solution an apolar organic solvent until the phosphoramidite forms a gum phase that is discrete from the organic solution; and
   (c) separating the organic solution from the gum phase, said gum phase containing a purified phosphoramidite.

70. A process of claim 69, optionally comprising repeating steps (a)–(c) from about 1 to about 3 times.

71. The process of claim 70, wherein the slightly polar organic solvent comprises toluene.

72. The process of claim 71, wherein the apolar organic solvent is selected from hexane and heptane.

73. The process of claim 72, wherein the apolar organic solvent is separated from the gum phase by decanting.

* * * * *

UNITED STATES PATENT AND TRADEMARK OFFICE
CERTIFICATE OF CORRECTION

PATENT NO.       : 7,030,230 B2                                                Page 1 of 1
APPLICATION NO.  : 10/280383
DATED            : April 18, 2006
INVENTOR(S)      : Bruce Ross et al.

It is certified that error appears in the above-identified patent and that said Letters Patent is hereby corrected as shown below:

1) Column 44, line 26, please delete "HO" and insert therefore --OH--;

2) Column 47, line 55, please delete "thither" and insert therefore --further--;

3) Column 48, lines 6-14, please delete " 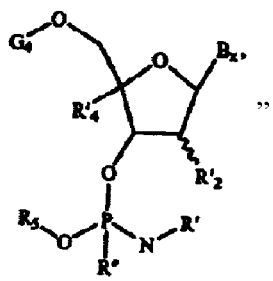 "

and insert therefore -- 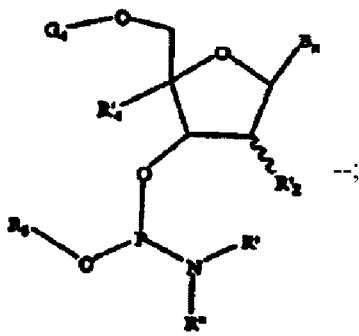 --;

4) Column 48, line 32, please delete "R6" and insert therefore --$R_6$--.

Signed and Sealed this

Seventeenth Day of October, 2006

JON W. DUDAS
*Director of the United States Patent and Trademark Office*